(12) United States Patent
Alonso et al.

(10) Patent No.: US 12,137,975 B2
(45) Date of Patent: Nov. 12, 2024

(54) SYSTEMS, METHODS, AND PROGRAM PRODUCTS FOR PERFORMING ON-OFF PERIMETRY VISUAL FIELD TESTS

(71) Applicant: Research Foundation for the State University of New York, Albany, NY (US)

(72) Inventors: José-Manuel Alonso, New York, NY (US); Mitchell Dul, Cold Spring, NY (US); Hamed Rahimi Nasrabadi, Brooklyn, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 696 days.

(21) Appl. No.: 17/217,553

(22) Filed: Mar. 30, 2021

(65) Prior Publication Data

US 2021/0298593 A1      Sep. 30, 2021

Related U.S. Application Data

(60) Provisional application No. 63/001,778, filed on Mar. 30, 2020.

(51) Int. Cl.
*A61B 3/024* (2006.01)
*A61B 3/00* (2006.01)
*A61B 3/113* (2006.01)

(52) U.S. Cl.
CPC ............ *A61B 3/024* (2013.01); *A61B 3/0025* (2013.01); *A61B 3/0041* (2013.01); *A61B 3/113* (2013.01); *A61B 2562/0219* (2013.01)

(58) Field of Classification Search
CPC ..... A61B 3/024; A61B 3/0025; A61B 3/0041; A61B 3/113; A61B 2562/0219; A61B 3/112; A61B 3/12
USPC ....................................................... 351/224
See application file for complete search history.

(56) References Cited

U.S. PATENT DOCUMENTS

| | | | |
|---|---|---|---|
| 2009/0018407 A1* | 1/2009 | Jung | A61B 3/113 705/2 |
| 2013/0141697 A1* | 6/2013 | Berry | G16H 10/60 351/242 |
| 2013/0155376 A1* | 6/2013 | Huang | A61B 3/024 351/224 |

(Continued)

*Primary Examiner* — Mohammed A Hasan
(74) *Attorney, Agent, or Firm* — Lance D. Reich; Peter Fallon

(57) ABSTRACT

Systems for performing ON-OFF perimetry visual field tests. The systems may include a display apparatus including at least one display, and at least one computing device in electronic communication with the display apparatus. The computing device(s) may be configured to perform the ON-OFF perimetry test on a patient by performing processes including directing the patient to visual focus on an eye fixation region depicted in a visual field. The visual field may be divided into a right side and a left side. The processes performed by the computing device(s) may also include generating a plurality of stimuli in the visual field to be detected by the patient, directing the patient to indicate when the patient detects each stimulus depicted within the visual field, and analyzing the patient's indications to diagnosis a retinal disease, a visual cortex disease, and/or a deficit condition of an eye of the patient.

20 Claims, 19 Drawing Sheets

(56) References Cited

U.S. PATENT DOCUMENTS

| | | | |
|---|---|---|---|
| 2015/0190048 A1* | 7/2015 | Huang ................ | A61B 3/0033 |
| | | | 351/239 |
| 2019/0094552 A1* | 3/2019 | Shousha ............... | A61B 3/024 |
| 2019/0222817 A1* | 7/2019 | Abou Shousha ...... | H04N 9/646 |

* cited by examiner

SYSTEMS, METHODS, AND PROGRAM PRODUCTS FOR PERFORMING ON-OFF PERIMETRY VISUAL FIELD TESTS

CROSS-REFERENCE TO RELATED APPLICATIONS

This application claims priority to U.S. provisional application No. 63/001,778 filed on Mar. 30, 2020, the content of which is hereby incorporated by reference into the present application.

RIGHTS IN THE INVENTION

This invention was made with government support under grant numbers EY027361 and EY005253 awarded by the National Institutes of Health. The government has certain rights in the invention.

FIELD

One or more aspects of the present disclosure relate to the detection of visual deficits, as well as retinal and visual pathway disease through an ON-OFF Perimetry Test.

BACKGROUND

Since the days of Leonardo da Vinci and Galileo Galilei it has been clear that human perception of dark features and light features are asymmetric. Early studies reported lower thresholds for the detection of dark stimulus than light stimulus and showed that light stimulus on dark backgrounds appear larger than similar-sized dark stimulus on light backgrounds.

It is now known that the visual cortex processes visual information stemming from two parallel pathways, the ON-pathway, which signals light increments or light stimuli, and the OFF-pathway, which signals light decrements or dark stimuli. Light increments and decrements are functions of time, which assume a temporal change from dark to light, in the case of light increments, or light to dark, in the case of light decrements. Whereas, light and dark stimuli are time independent and merely refer to stimuli that are lighter than the background, in the case of light stimuli, or darker than the background, in the case of dark stimuli.

The ON-pathway and OFF-pathway first combine in the primary visual cortex, at which point cortical neurons receive input from both pathways. Prior to arrival in the visual cortex, the ON-pathway and OFF-pathway are segregated in the thalamus. Even after combining in the visual cortex, these pathways remain segregated in different cortical domains.

Within this signaling framework, the asymmetry between dark and light stimuli is most pronounced in the visual cortex. It is also significant in the retina and is thought to originate in photoreceptor outputs. Research has shown that cortical responses to dark stimuli are stronger, faster, have better spatial and temporal resolution, are more linearly related to luminance contrast, and are driven by a larger number of cortical neurons than responses to light stimuli. Moreover, dark targets are detected faster and more accurately on noisy backgrounds, and dark pixels are more important in judging texture variance.

Perimetry is a systematic measure of visual field function, the area where stimuli can be seen in peripheral vision while the eye is fixed on a central point. In clinical settings, e.g. neurology, optometry, and ophthalmology, perimetry testing is commonly used to detect and map declines in peripheral vision for diagnostic and treatment purposes.

Currently, standard automated perimetry (aka static automated perimetry or "white-on-white perimetry") is the most commonly used form of visual field testing. In this form of perimetry, threshold values are determined by projecting white stimuli on a white background. A conventional system or machine for conducting standard automated perimetry on a person is shown in FIG. 1A.

White-on-white perimetry is marred by the following limitations: (i) inability to measure deficits in OFF-pathway function; and (ii) administration at specialized eye clinics. In concert, these limitations greatly constrain the efficacy and utility of the technology, as well as the ability of different patient populations to take advantage of the technology.

The first limitation of white-on-white perimetry is that, though it is well-suited to measure ON-pathway cortical responses, it is unable to measure deficits in OFF-pathway function.

This is problematic because deficits in OFF-pathway function are important in monitoring the progression, and treatment, of diseases, such as glaucoma—a group of eye conditions where damage to the optic nerve causes irreparable vision loss. Glaucoma is best known as a leading cause of blindness for people over the age of 60 but can occur in individuals at any age. Often times, glaucoma presents without warning signs and with effects so gradual that a change in vision may not become noticeable until the disease is advanced. Experiments in animal models of glaucoma suggest that the OFF pathway may be affected sometimes earlier than the ON-pathway in the retina. However, white-on-white perimetry is not optimized for detecting early stage glaucoma deficits in OFF-pathway function.

In addition to glaucoma, amblyopia is another eye disease that affects both the ON-pathway and OFF-visual pathway. Amblyopia, or colloquially known as lazy eye, is a vision development disorder common in children where one eye fails to achieve normal visual acuity. Normally, the brain uses signals from both eyes for vision. In amblyopia patients, the nerve pathways between a thin layer of tissue (retina) at the back of the eye and the brain are disrupted or changed leading to weakening of visual acuity in one eye. Eventually, the eyes' ability to work together decreases, the brain suppresses or ignores input from the weaker eye and relies only on the stronger eye. Similar to glaucoma, amblyopia affects both ON and OFF visual pathways.

The second limitation of white-on-white perimetry is that it can only be administered at specialized eye clinics; it cannot be administered in homes. As a consequence of this, it is ineffectual for immobile or poorly mobile populations and is poorly adapted for gaming applications. In addition, this limitation of white-on-white perimetry makes it largely inaccessible to populations in regions with poor access to medical resources. Based on the European Glaucoma Society (EGS) guidelines and statistical modeling of visual-field data, newly diagnosed glaucoma patients should undergo perimetry testing three times per year in the first 2 years after initial diagnosis. However, many patients and clinicians are raising concerns about the feasibility of increasing the frequency of perimetry testing due to the lack of financial and personnel resources to deliver the tests and services.

Two other species of perimetry, Short-Wavelength Automated Perimetry ("SWAP") and Frequency Doubling Technology ("FDT"), are also of note.

SWAP, or blue-yellow perimetry, projects a blue stimulus on a yellow background. SWAP was designed to detect early visual field loss before a reduction in differential light sensitivity can be seen using white-on-white perimetry, however, it has several limitations, including, but not limited to the following: (i) it has higher test-retest variability than white-on-white; (ii) it is influenced by media opacities; and (iii) it has a higher testing time, which makes it less preferable to patients and less efficient in practice.

FDT combines low spatial frequency and high temporal frequency (theoretically) target ganglion cells of the magnocellular pathway. FDT has been shown to have a high sensitivity and selectivity for early detection of glaucoma. However, unlike SWAP, topographical representation and extent of the defect detection is limited, which makes it more difficult to identify subtle defects and monitor change over time in glaucoma progression. These limitations are amplified by the FDT limited testing patterns. FDT is also influenced by the presence of media opacities and other causes of decreased retinal illuminance.

Therefore, new technological advancements and new methods are needed to address the shortcomings in the currently used methods for measuring visual deficits in the OFF-pathway and ON-pathway.

SUMMARY

The following is a summary of the disclosure in order to provide a basic understanding of its novelty. This summary is not intended to identify all key or critical elements of the disclosure or to delineate the entire scope of the disclosure. Its primary purpose is to present some concepts of the disclosure in a simplified form as a prelude to the more detailed description that is presented later.

Reference throughout this specification to "one embodiment," "an embodiment" or a non-limiting example means that a specific feature, structure, or characteristic described in connection with an embodiment is included in at least one embodiment of claimed subject matter. Thus, appearances of phrases such as "in one embodiment" or "an embodiment" in various places throughout this specification are not necessarily all referring to the same embodiment. Furthermore, specific features, structures, or characteristics may be combined in one or more embodiments.

The present disclosure includes a novel method to measure and characterize visual deficits in the ON-pathway and OFF-pathway in diseases affecting the retina, visual cortex, and other components of the visual pathway. Specifically, the disclosure discloses a method for performing an ON-OFF perimetry visual field test, by directing a subject or patient to focus on a fixation point at the center of the visual field, which is divided into a right side and left side, and to detect a dark or light stimulus when it appears in the visual field. The patient detects a stimulus by pressing the button in the hand corresponding to the side of the visual field where the stimulus was detected i.e. pressing push-button in right hand when stimulus appears on the right side of the visual field. The ON-OFF perimetry test disclosed, herein, has multiple tracking components for eye position, head position, blinks and pupil diameter. Patients' ability to correctly detect light and dark stimulus or inability to detect the light and dark stimulus is used to identify deficits in ON-pathway and OFF-pathway and subsequent progression of certain eye diseases. ON-OFF Perimetry disclosed herein includes further variations, including but not limited to, finer sampling of scotomas, slow-moving stimuli, and increasing stimulus size to make it more reliable in its ability to become a valuable diagnostic tool in the eye clinic.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure, in which.

It is noted that the drawings of the disclosure are not to scale. The drawings are intended to depict only typical aspects of the disclosure, and therefore should not be considered as limiting the scope of the disclosure. In the drawings, like numbering represents like elements between the drawings.

DETAILED DESCRIPTION

These, and other, aspects and objects of the present disclosure will be better appreciated and understood when considered in conjunction with the following description and the accompanying drawings. It should be understood, however, that the following description, while indicating preferred embodiments of the present disclosure and numerous specific details thereof, is given by way of illustration and not of limitation. Many changes and modifications may be made within the scope of the present disclosure without departing from the spirit thereof and the disclosure includes all such modifications.

The ON-OFF perimetry visual field test described herein monitors eye and head position, pupil diameter, stimulus onset, subject response, and other variables to diagnose retinal, visual cortex, and other visual diseases and conditions. Initially, embodiments of this test may focus on detecting visual loss for use in diagnosing diseases like glaucoma and amblyopia.

Figure 1A:
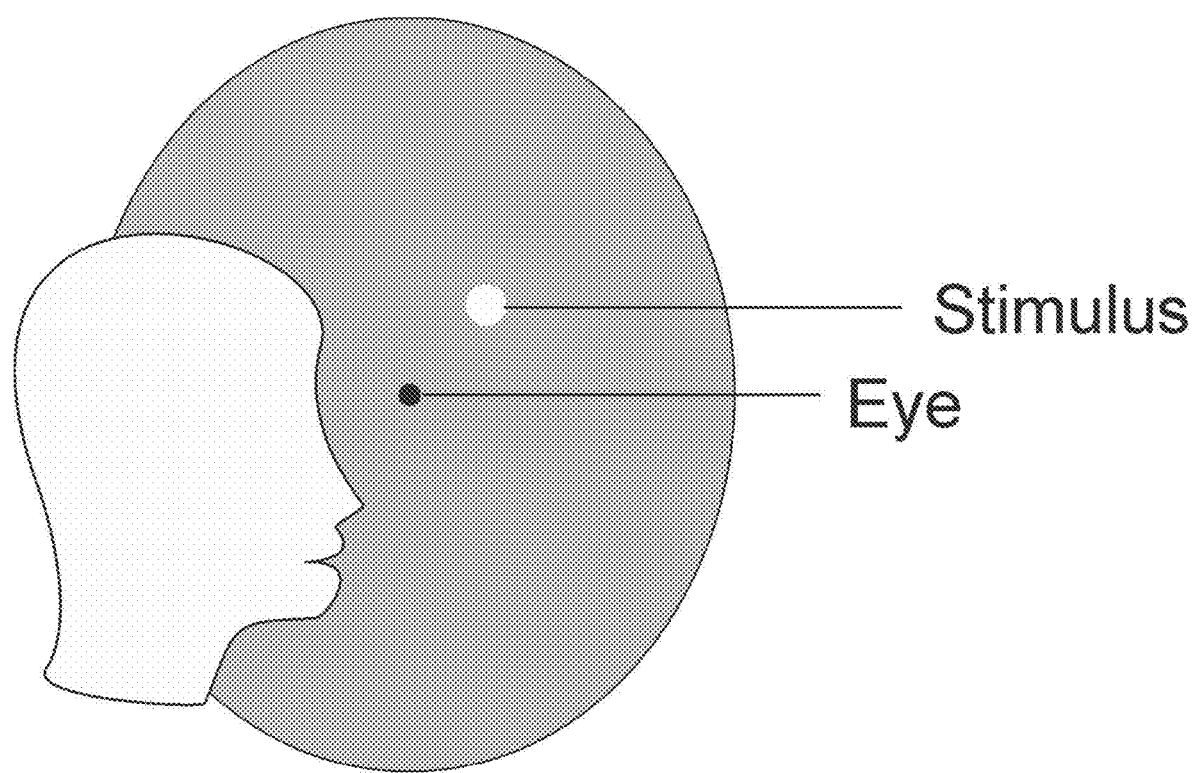
FIG. 1A depicts a prior art setup for white-on-white perimetry, according to embodiments of the disclosure.
Figure 1B:
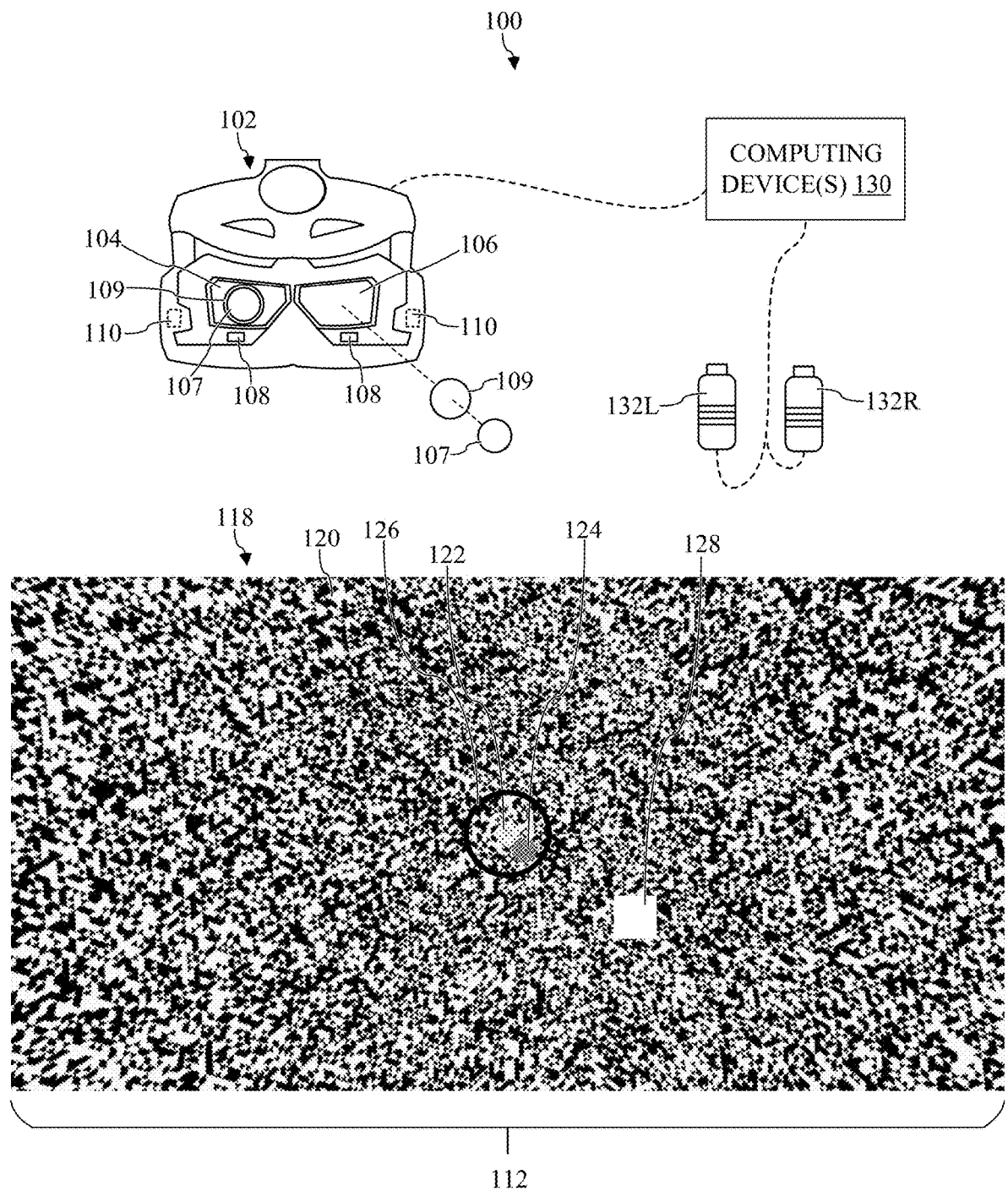
FIG. 1B shows a schematic view of a system used to perform ON-OFF perimetry visual field tests, according to embodiments of the disclosure.

As depicted in FIG. 1B, the ON-OFF perimetry system 100 (hereafter, "system 100") may include a head mounted display apparatus 102 (hereafter, "display apparatus 102"). In the non-limiting example, display apparatus 102 may be coupled to and/or positioned on a patient's head and substantially cover/interact with the patient's eyes during the ON-OFF perimetry field test discussed herein. Display apparatus 102 may be formed from any suitable head mounted and/or personal display apparatus or device that may provide various visual cues to a user or patient when performing an ON-OFF perimetry field test, as discussed herein. In one non-limiting example, display apparatus 102 may be formed from an HTC Vive head mount device.

Display apparatus 102 of system 100 may also include a plurality of displays 104, 106. More specifically, display apparatus 102 may include a plurality of visual displays 104, 106 formed integrally therein. In the non-limiting example, a first display 104 may correspond to and/or may be aligned with a patient's left eye, while second display 106 may correspond to and/or may be aligned with a patient's right eye. As such, first display 104 may be positioned adjacent to, but separated from, second display 106 within display apparatus 102. Each of the plurality of displays 104, 106 may be formed from and/or may include any suitable visual display, screen, and/or graphical interface that may display or provide a visual/graphical representation of various features associated with the ON-OFF perimetry field test, as discussed herein. In non-limiting examples, each of the plurality of displays 104, 106 may include a refresh rate of approximately 90 Hz, and a dynamic range from, for example, approximately 1 cd/m$^2$ to approximately 150 cd/m$^2$, which allows assessing a visual field of a patient under a large variety of daylight (e.g., photopic) conditions when performing the ON-OFF perimetry field test using system 100, as discussed herein.

As shown in FIG. 1B, display apparatus 102 of system 100 may also include interchangeable lenses 107. Lenses 107 may be positioned between the patient's eye and displays 104, 106. More specifically, an individual lens 107 may be positioned in front of, adjacent to, and/or over one of the two displays 104, 106 included in display apparatus 102. As shown in FIG. 1B, one lens 107 may be positioned adjacent display 104, while another lens 107 may be removed from and/or shown in an exploded view for display 106. In a non-limiting exam lenses 107 may be inserted into display apparatus 102 and may be held in place within display apparatus using a support frame 109. Support frame 109 may receive and/or may be secured to lenses 107, and may subsequently be inserted into display apparatus 102 to hold or position lenses within display apparatus 102, between displays 104, 106 and the patient's eye during the ON-OFF perimetry visual field tests discussed herein. Lenses 107 may be customizable and/or identical to the glasses prescription for the patient utilizing display apparatus 102 during the ON-OFF perimetry visual field tests. Including lenses 107 and support frames 109 may allow a user to perform the test discussed herein without having to wear their prescription glasses and/or contact lenses. In a non-limiting example, lenses 107 may also include an anti-reflective coating covering a surface. In non-limiting examples, the anti-reflective coating may cover or coat the surface of lenses 107 positioned directly adjacent or closes to display 104, 106, and/or the surface of lenses 107 positioned adjacent the patient's eye. Although shown as only covering a portion of displays 104, 106 of display apparatus 102, lenses 107 may alternatively be sized to cover the entirety of displays 104, 106.

Display apparatus 102 of system 100 may include an eye tracking system 108. As shown in FIG. 1B, eye tracking system 108 may be positioned within display apparatus 102. Eye tracking system 108 may also be positioned within display apparatus substantially adjacent displays 104, 106. Eye tracking system 108 may be formed from any suitable device(s), assembly, and/or system that may be configured to at least monitor or detect a patient's eye position and/or pupil diameter during the ON-OFF perimetry field test discussed herein. For example, eye tracking system 108 may be formed as a Tobii eye tracking system formed within display apparatus 102. In the non-limiting example, eye tracking system 108 may include two distinct devices, components, and/or sensors that may monitor a patient's eye position and/or pupil diameter, as discussed herein. However, it is understood that eye tracking system 108 may include more or less devices, components, and/or sensors formed within display apparatus 102 to perform eye tracking processes (e.g., eye position, pupil diameter) during the ON-OFF perimetry field test.

Additionally, display apparatus 102 may include a gyroscope and/or accelerometer 110 (shown in phantom). More specifically, display apparatus 102 of system 100 may include a gyroscope/accelerometer 110 positioned therein/thereon. Gyroscope/accelerometer 110 may be formed as any suitable gyroscope/accelerometer that may detect, determine, and/or monitor head rotation when performing the ON-OFF perimetry field test, as discussed herein.

Although shown and discussed herein as a personal-patient headset that may be coupled to/positioned directly on a patient's head during the ON-OFF perimetry field test, it is understood that display apparatus 102 of system 100 may include a distinct configuration. For example, rather than being mounted directly to the patient's head, display apparatus 102 may be affixed to and supported by a surface (e.g., tabletop). In this example, the patient may move their head to engage the apparatus 102 and/or view displays 104, 106 during the ON-OFF perimetry field test. In another non-limiting example, display apparatus 102 may be mounted to a movable arm. During the ON-OFF perimetry field test, the movable arm may be moved to contact a patient's face directly in order for the patient view displays 104, 106 and perform the ON-OFF perimetry field test.

During the ON-OFF perimetry field, test displays 104, 106 of display apparatus 102 may depict, display, present, and/or provide a visual field 112. Visual field 112 may include or depict the graphic/visual representation of various features to a patient in order to perform the ON-OFF perimetry field test. That is, visual field 112 may be displayed by and/or generated within each of the plurality of displays 104, 106 included in display apparatus 102, and may provide, present, display, and/or depict various features discussed herein to the patient while performing the ON-OFF perimetry field test. For example, visual field 112 may include a "noisy" background 118 (hereafter, "background 118"). Background 118 may be formed from a plurality of contrasting color shapes. In the non-limiting example shown in FIG. 1B, background 118 included in visual field 112 displayed by display(s) 104, 106 may be formed from and/or may include a plurality of equidistant triangles 120. Triangles 120 forming background 118 may be formed, configured, and/or displayed in a way such that the resulted geometry becomes a sphere centered around the observer within approximately a 2-meter distance. The use of triangles 120 may facilitate the mathematical reconstruction of a spherical background implemented with, for example, an algorithm. Additionally, and although shown in FIG. 1B as being black and white triangles, the plurality of equidistant triangles 120 forming background 118 may also be black and gray triangles 120. In other non-limiting examples, triangles 120 forming background 118 may be formed from any two distinct and/or contrasting colors.

In a non-limiting example shown in FIG. 1B, triangles 120 may have approximately 0.5 degrees per side, but may include larger or smaller configurations and/or geometric constructions/characteristics (e.g., approximately 0.05 to approximately 2.5 degrees) depending, at least in part, on characteristics of the ON-OFF perimetry field test being performed. For example, when using triangles of 0.5 degrees/side, the resulting sphere is formed by 131072 triangles, which provides 131072 degrees of freedom for constructing background 118 by changing the intensity of each triangle 120, separately. The example design, construction, and/or configuration of background 118 shown in FIG. 1B may enable the performance of white-on-white perimetry by having all triangles with the same gray/light color intensity while allowing for more complicated and dynamic backgrounds. The size of triangles 120 may also be upscaled by a factor of two (1 deg., 2 deg., and etc.). However, the smallest size is used to achieve the highest possible degrees of freedom and provide finer sampling of the visual field, as discussed herein.

Although shown to be formed from triangles 118, it is understood that background 118 may be formed from a pattern of a plurality of distinct shapes and/or geometries. For example, system 100 may also use shapes/geometries to form background 118 including, but not limited to, pentagons, hexagons or any shape that can be made with equidistant triangles. In other non-limiting examples, background 118 may be formed using spherical polyhedron geometries that allow spherical tiling. In additional examples background 118 may be formed as a predetermined, predefined, and/or selectable, stock image.

As discussed herein, background 118 may achieve a higher degree of freedom resulting in an improved ON-OFF perimetry visual field test. For example, inhomogeneous background 118 with an average gray level intensity may be used to excite ON or OFF pathways using light or dark stimuli during the test, as discussed herein. Furthermore, and as discussed herein, accurately mapping and diagnosing the defects in the signaling of the visual pathways for a patient during ON-OFF perimetry testing may require understanding inherent sources of the noise in system 100. Regardless of difficulties in estimating the noise level, artificially producing noise could leverage the signal estimation since the given value of noise level can be controlled. The ON-OFF perimetry produces an artificial background noise by randomly setting the brightness of the embedded triangles 120 to light or dark levels in background 118. This also ensures that the average light intensity lies in the middle of the dynamic range which could produce both ON and OFF signals.

Visual field 112 displayed by displays 104, 106 of display apparatus 102 may also include a central eye fixation point or region 122 (hereafter, "eye fixation region 122"). Eye fixation region 122 may include a dot, a point, or a predetermined geometry that may be included, depicted, provided, and/or visible in visual field 112 during the ON-OFF perimetry field test, as discussed herein. Although shown as including a hatched pattern, in non-limiting examples, eye fixation region 122 included in visual field 112 may be formed from a different color than the contrasting colors forming background 118. As such, eye fixation region 122 may be more readily visible to a patient undergoing the ON-OFF perimetry field test. Additionally, eye fixation region 122 may also be formed from a distinct geometry and/or shape than background 118 to increase visibility/ease of identification against "noisy" background 118 when performing the ON-OFF perimetry visual field test. In the non-limiting example shown in FIG. 1B, eye fixation region 122 may be centrally located and/or positioned within visual field 112. In other non-limiting examples, eye fixation region 122 may be positioned "off-center" and/or may not be centrally located on background 118 depicted in visual field 112. In this example, eye fixation region 122 may be "off-center" in order to test/analyze one side of a patient's peripheral vision when performing the ON-OFF perimetry visual field test. For example, to test a larger area of a patient's right-side peripheral vision during a monocular testing process, eye fixation region 122 may be moved or positioned to the left-of-center of visual field 112. As discussed herein, eye fixation region 122 may be focused on by a patient undergoing the ON-OFF perimetry field test to initial calibrate the eye position of the patient prior to performing the ON-OFF perimetry field test, as well as provide a focal point for the patient when performing the ON-OFF perimetry field test.

Additionally as shown in FIG. 1B, visual field 112 may further include an eye tracking point 124. Eye tracking point 124 may a visual representation on visual field 112 of the monitored eye fixation and/or movement of the patient's eye as determined by eye tracking system 108 of display apparatus 102. That is, eye tracking point 124 may be generated and/or visually displayed in visual field 112 as a real-time representation of movement in the patient's eye(s) as they focus on eye fixation region 122 during the ON-OFF perimetry visual field test. In a non-limiting example, eye tracking point 124 may allow the patient to monitor the quality of their own visual fixation (e.g., fixation on eye fixation region 122) as they perform the ON-OFF perimetry visual field test, as discussed herein. Similar to eye fixation region 122, although shown as including a hatched pattern, eye tracking point 124 included in visual field 112 may be formed from a different color than the contrasting colors forming background 118. Eye tracking point 124 may also be a different color than eye fixation region 122 to allow the patient to distinguish between the two features included in visual field 112. Additionally, eye tracking point 124 may also be formed from a distinct geometry and/or shape than background 118 to increase visibility/ease of identification against "noisy" background 118 when performing the ON-OFF perimetry visual field test.

In the non-limiting example shown in FIG. 1B, visual field 112 may include an eye fixation control region 126. Eye fixation control region 126 may substantially surround and/or encompass eye fixation region 122. For example, and as shown in FIG. 1B, eye fixation control region 126 may be defined by a circle that substantially surrounds eye fixation region 122. Although shown as a circle, it is understood that visual field 112 may include any geometry and/or shape to define eye fixation control region 126. Eye fixation control region 126 may define/represent, for example, an area or bound of a patient's central vision based on the patient's point of visual fixation—eye fixation region 122. As such, the remaining portion of visual field 112 outside of eye fixation control region 126 may define/represent the patient's peripheral or indirect vision. During the ON-OFF perimetry visual field test, a patient may be instructed to keep their visual focus point on eye fixation region 122, and more specifically, to keep eye tracking point 124 within eye fixation control region 126 to improve the results/finds based on the visual field test performing using system 100. As discussed herein, when the patient's eye/vision is tracked and/or detected outside of eye fixation control region 126, the data collected at that time during the test may be discarded/rejected. That is, the ON-OFF perimetry visual field tests may automatically reject any data collected when the patient's eye position is not within eye fixation control region 126. To obtain the desired or predetermined amount of data required by the ON-OFF perimetry visual field tests, the stimulus presentations may be repeated for the rejected data.

Visual field 112 displayed by displays 104, 106 of display apparatus 102 may also include a stimulus 128. In the non-limiting example, a light or white stimuli is shown, depicted, provided, and/or visible within visual field 112. However, and as discussed herein, stimuli 128 visible within visual field 112 during ON-OFF perimetry visual field tests may be dark or black as well (see, FIGS. 2B-2F). The color of stimuli 128 may be dependent, at least in part, on characteristics of the ON-OFF perimetry visual field tests being performed. In non-limiting examples, the light stimuli 128 may match the light color of the shapes/geometries forming a portion of background 118, while the dark stimuli 128 may match the dark color of the shapes/geometries forming the remaining portion of background 118. In other non-limiting examples, the light stimuli 128 and dark stimuli 128 may be a distinct shade and/or intensity of the colors for the geometries/shapes forming background 118. Additionally as shown in the non-limiting example, stimuli 128 may be formed as a square. In other non-limiting examples, stimuli 128 may be formed from other shapes, geometries, and/or images including, but not limited to, circles, pentagons, hexagons, any shape that can be made with equidistant triangles, or spherical polyhedron geometries. In additional examples, and similar to the background, stimuli 128 may also be formed as a predetermined, predefined, and/or selectable, images. In the non-limiting examples where stimuli 128 are formed in geometries using equidistant triangles, the triangles forming stimuli 128 may include configurations and/or geometric constructions/characteristics that are between approximately 2.5 degrees/side and approximately 4.0 degrees per side. In other non-limiting examples, the configurations and/or geometric constructions/characteristics may be at minimum approximately 0.05 degrees/side and approximately 0.4 or larger for stimuli 128. The limits may include the lower limits for stimuli 128 that may be visually detectable by a patient's fovea-vision and periphery-vision, respectively.

When performing one non-limiting example of the ON-OFF test, and as discussed herein, a dark or light stimuli 128 may be presented in visual field 112 while the patient's eyes or vision are fixating on eye fixation region 122 and/or within eye fixation control region 126. Stimuli 128 are chosen to be formed as, for example, squares with the size increased with visual eccentricity distance by a power law function. The increase in size may compensate for lower spatial sampling in the peripheral vision and the parameters of the power law functions may be determined to achieve the consistent performance over various points of visual field 112 during the ON-OFF perimetry visual field test. The ON-OFF perimetry visual field test may accomplish improved visual field mapping compared to other task variations/test characteristics (e.g. detect larger stimuli). However in other non-limiting examples, some variations may allow detecting subtler visual deficits (e.g. dimmer or smaller stimuli) (see, FIGS. 5 and 6).

System 100 shown in FIG. 1B may also include at least one computing device 130. Computing device(s) 130 may be a stand-alone system, or alternatively may be a portion and/or included in a larger computing device (not shown) of system 100. For example, and as shown in FIG. 1B, computing device(s) 130 may be positioned outside of display apparatus 102 as its own system. Alternatively, computing device(s) 130 may be part of the overall computing system that is used in and included within display apparatus 102 of system 100. As discussed herein, computing device(s) 130 may be configured to generate, create, and/or run the various ON-OFF perimetry visual field tests performed using system 100. Additionally, computing device(s) 130 may be configured to receive input and/or patient-data during the ON-OFF perimetry visual field tests. As shown in FIG. 1B, computing device(s) 130 may be in electronic communication with, electrically coupled, operatively coupled, and/or communicatively coupled to various devices, apparatuses, and/or portions of system 100. In non-limiting examples, computing device(s) 130 may be hard-wired and/or wirelessly connected to and/or in communication with system 100, and its various components via any suitable electronic and/or mechanical communication component or technique. For example, computing device(s) 130 may be in electronic communication/operatively coupled to display apparatus 102. Computing device(s) 130 may be in communication with display apparatus 102 to provide data related to and/or to run ON-OFF perimetry visual field tests using displays 104, 106 of display apparatus 102. As such, visual field 112, and the features included therein (e.g., eye fixation region 122, eye fixation control region 126, etc.) may be generated by computing device(s) 130, and the data/program product stored therein (e.g., Unity virtual reality engine). Additionally, and as discussed herein, computing device(s) 130 may also receive, process, and/or analyze data received from display apparatus 102 during the ON-OFF perimetry visual field tests. For example, computing device(s) 130 may receive data obtained by eye tracking system 108 relating to the movement/position of the patient's eyes during the ON-OFF perimetry visual field tests.

System 100 may also include at least one remote 132. In the non-limiting example, system 100 may include two remotes 132L, 132R. As shown in FIG. 1B, remotes 132L, 132R may be in electrical communication, mechanical communication, operatively coupled, and/or electronically coupled to computing device(s) 130. Remotes 132L, 132R may be used during the ON-OFF perimetry visual field test to allow a user to identify which side of visual field 112 stimuli 128 may be depicted and/or visually detected. That is, first remote 132L may correspond to an indication/detection of stimuli 128 be provided/shown on a left side of visual field 112 during the ON-OFF perimetry visual field test, and second remote 132R may correspond to an indication/detection of stimuli 128 be provided/shown on a right side of visual field 112. As discussed herein, the patient may engage and/or interact with the remotes 132L, 132R to indicate that they have seen a provide stimuli 128, and also where/which side the stimuli 128 was depicted. As such, and as discussed herein, it is understood that during the ON-OFF perimetry visual field test, visual field 112 may be divided into a "left side" and a "right side," where stimuli 128 may be visual displayed to either side and subsequently detected by the patient. The detection of stimuli 128 and associated data generated by the patient engaging remotes 132 may be provided directly to computing device(s) 130 for processing/analysis. Remotes 132 of system 100 may be any suitable device, component, and/or apparatus that may allow a patient to provide an indication that a stimuli 128 has been detected during the ON-OFF perimetry visual field test.

In other non-limiting examples, system 100 may not include remotes 132. Rather, during the ON-OFF perimetry visual field test, a patient may raise their left/right hand and/or tilt their head to indicate which side stimuli 128 is depicted/visualized within visual field 112.

Although depicted herein as a single system 100 that may be incorporated and/or located in a single transmission, it is understood that system 100 may be formed and/or located in distinct locations and may communicate/provide data using suitable data transmissions/communication networks. For example, display apparatus 102 and remotes 132 may be located within a patient's home, while computing device(s) 130 may be located at a central server and/or single data collection location. In the non-limiting example, computing device(s) 130 may communicate with display apparatus 102 and remotes 132 wirelessly (e.g., over internet, cloud networking) as discussed herein, such that a patient may conduct the ON-OFF perimetry visual filed test within the comfort of their own home, and their doctors may subsequently be sent, obtain, and/or receive the test data from the computing device(s) 130 in real-time or after the test.

Turning to FIGS. 2A-2F, the process of performing a non-limiting example of an ON-OFF perimetry visual field test to measure deficits in the ON and OFF visual pathways for a patient may be shown. The process of performing ON-OFF perimetry visual field test may be described herein with reference to visual field 112 and the various features included therein (e.g., eye fixation region 122, eye fixation control region 126, stimuli 128, etc.). It is understood that similarly numbered and/or named components may function in a substantially similar fashion. Redundant explanation of these components has been omitted for clarity.

It is noted that the process of performing ON-OFF perimetry visual field test as discussed herein with respect to FIGS. 2A-2F may be a monocular, or single eye, visual field test. For example, the test discussed herein may be performed to measure the deficits in ON and OFF visual pathways and/or to identify glaucoma in a patient by performing the test on each eye individually. However, system 100 may perform a binocular, or both eye, ON-OFF perimetry visual field test to detect deficits in a patient's vision. That is, display apparatus 102 providing visual field 112 may allow for stimuli 128 to be presented monocularly, binocularly, or alternating between different monocular and binocular conditions that would allow for visual field tests to be performed on patient eyes. As discussed herein, the stimuli 128 may be superimposed in noise (e.g., background 118) to allow testing the patient's visual system under challenging environments to help identify visual deficits. For example, varying the amount of noise (and difficulty of visual detection) by altering background 118 of visual field 112 may help to better identify subtle visual deficits for a patient.

Figure 2A:
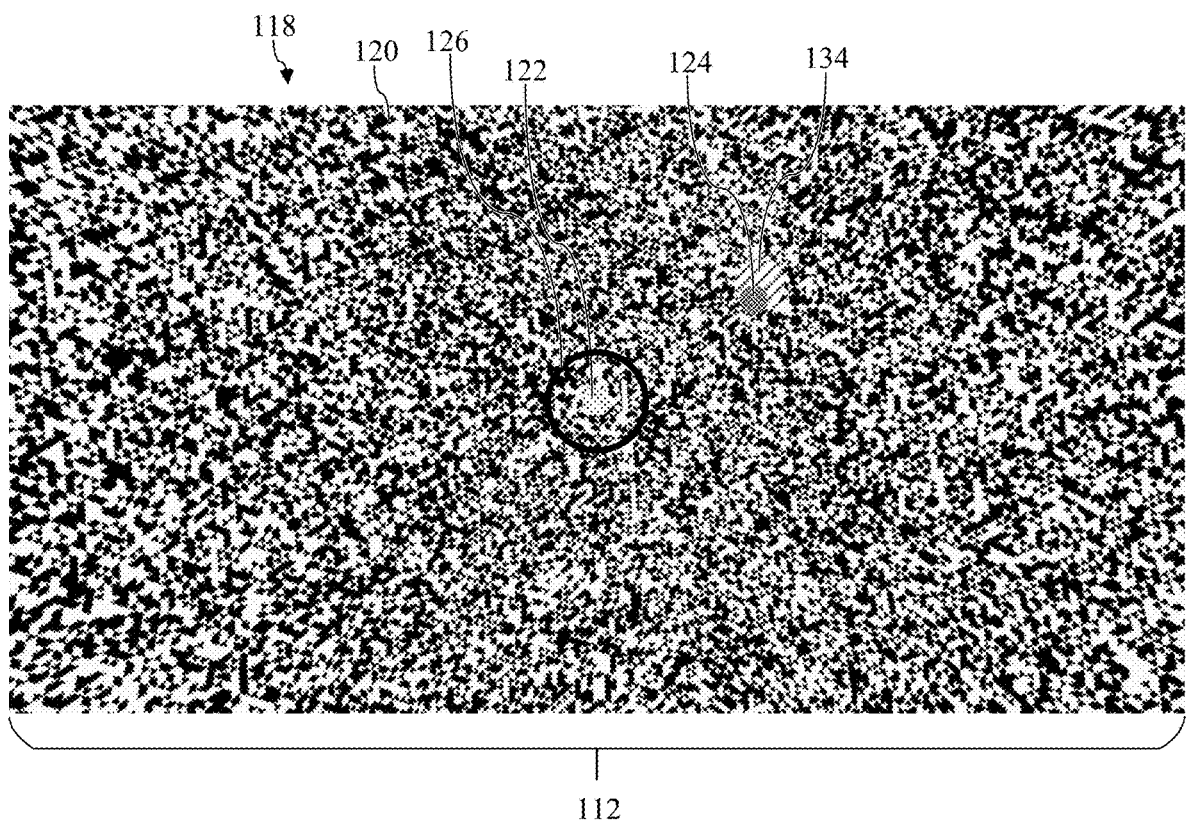
FIGS. 2A-2F show illustrative views of a visual field generated by a display apparatus of the system of FIG. 1 depicting a process for performing ON-OFF perimetry visual field tests, according to embodiments of the disclosure.

To measure the deficits in the ON and OFF visual pathways, a series of steps may be performed by the patient. The initial step in the ON-OFF perimetry visual field test may include performing an eye movement calibration procedure. As shown in FIG. 2A, eye movement calibration procedure may include providing/depicted eye fixation region 122, and eye fixation control region 126 in visual field 112. During the eye movement calibration, the patient is asked to fixate or focus their eye(s) on a calibration target 134 which may move or change between a predetermined number of distinct positions within visual field 112 during the calibration procedure. In a non-limiting example, calibration target 134 may move to five (5) distinct positions within visual field 112. As calibration target 134 becomes visible in each distinct position within visual field 112, eye tracking system 108 of display apparatus 102 (see, FIG. 1B) may track the movement of the patient's (eye), and may estimate eye movements to any position within the visual field 112. In the non-limiting example shown in FIG. 2A, calibration target 134 may include or be formed as circle. In other non-limiting examples calibration target 134 may be formed from any geometry and/or shape, including a geometry/shape that may be distinct from the shapes forming background 118 to increase visibility/ease of identification against "noisy" background 118 when performing the eye movement calibration procedure. Although shown as including a hatched pattern, in non-limiting examples, calibration target 134 included in visual field 112 may be formed from a different color than the contrasting colors forming background 118. As such, calibration target 134 may be more readily visible to a patient.

Figure 2B:
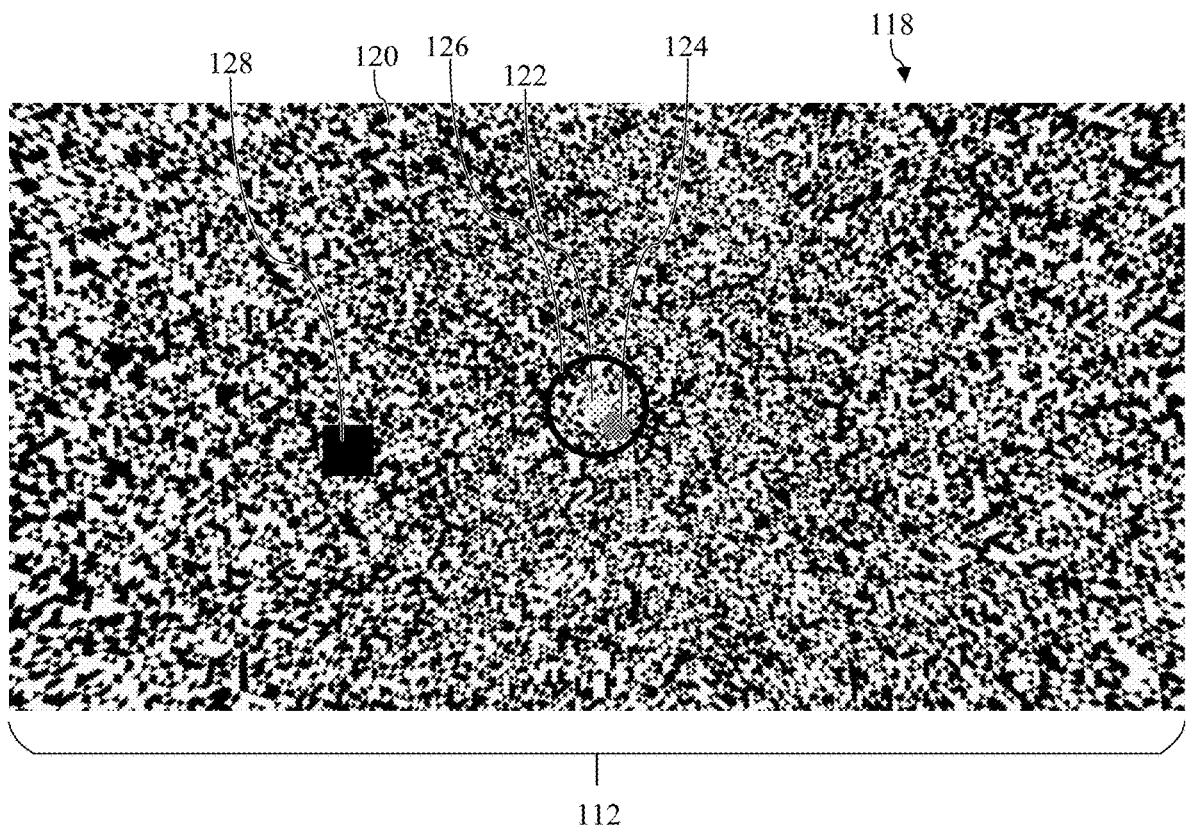

After the calibration, a series of stimuli 128, in the form of light and/or dark squares, may be displayed on a noisy background 118 of visual field 112. That is, a single stimulus 128 may be provided on visual field 112, in the patient peripheral vision (e.g., outside of eye fixation control region 126), for the patient's visual detection during the ON-OFF perimetry visual field test. When each stimulus 128 is provided to the patient during the test, the patient may be instructed to fixate or focus their vision on eye fixation region 122. The patient may continuously have their eye fixation monitored while performing test using eye tracking point 124, as discussed herein. While fixating their vision on eye fixation region 122, the patient may have a predetermined time to identify or visualize the single stimulus 128 and provide input or indication of seeing stimulus 128, via remotes 132, before a new, single stimulus 128 of the series of stimuli 128 is provided on visual field 112. Each individual stimulus 128 of the series of stimuli may be positioned in a distinct portion than the other stimulus 128. Additionally, each stimulus of the series of stimuli 128 may remain a single color (e.g., light or dark), may alternate between colors, may randomly including one of the two colors, or may undergo a predetermined sequence of being provided/visible as different colors. Turning to FIG. 2B, visual field 112 depicts a first stimulus 128 of the series of stimuli 128. Stimulus 128 may be depicted or provided on the left side of noisy background 118 during the ON-OFF perimetry visual field test. Additionally, visual field 112 may also include eye fixation region 122, an eye fixation control region 126, and eye tracking point 124. When visual field 112 includes stimulus 128 positioned or depicted in visual field 112 as shown in FIG. 2B, the patient may visually detect stimulus 128, and subsequently confirm the visual detection by provide input via remotes 132. Specifically, the patient may engage and/or interact with remote 132L to identify that the stimulus 128 was visually detected on the left side of visual field 112. However, if stimulus 128 is not visible to the patient and/or the patient does not engage remote 132 within a predetermined period of time, then ON-OFF perimetry visual field test may determine that stimulus "did not appear" to the patient as a result of a visual deficit (e.g., ON-pathway deficit, OFF-pathway deficit).

For example, if the patient does not engage remotes 132 within between approximately 1 to approximately 10 seconds, and more specifically between approximately 1 and approximately 3 seconds, e.g. 2 seconds, stimulus 128 depicted on visual field 112 will be marked as "not appearing." The patient may be aware that approximately 5% of the trials do not have a visible stimulus 128. This may ensure accuracy of responses submitted by the patient and subsequently optimizes the results of the ON-OFF perimetry visual field test.

As discussed herein, the patient is instructed to maintain their visual focus on eye fixation region 122, and more specifically to keep their eye focus within eye fixation control region 126 during the calibration and/or when detecting provided stimuli 128. Where the patient's eye remains focused on eye fixation region 122/within eye fixation control region 126, the data or input collected/received (e.g., engaging remote 132 to identify which side the stimuli 128 is provided) may be used to determine visual deficits and/or ocular diseases for the patient. However, when the patient's eye or visual focuses tracks outside of eye fixation control region 126 the data or input collected at that time may be discarded and/or rejected by computing device(s) 130. In this instance, the process of presenting stimuli 128 for visual detection by the patient may be repeated until computing device(s) 130/system 100 may collect a predetermined or desired number of data inputs. The predetermined or desired number of inputs may aid in determining and/or detecting vision deficits and/or diseases of the patient.

FIGS. 2C-2F may depict additional non-limiting examples of visual field 112 during ON-OFF perimetry visual field test. In each of the non-limiting examples, visual field 112 may include eye fixation region 122, an eye fixation control region 126, eye tracking point 124, and stimulus 128. Additionally, and with comparison to each of FIGS. 2C-2F, the position, size, and/or color of stimuli 128 may differ from figure to figure.

Figure 2C:
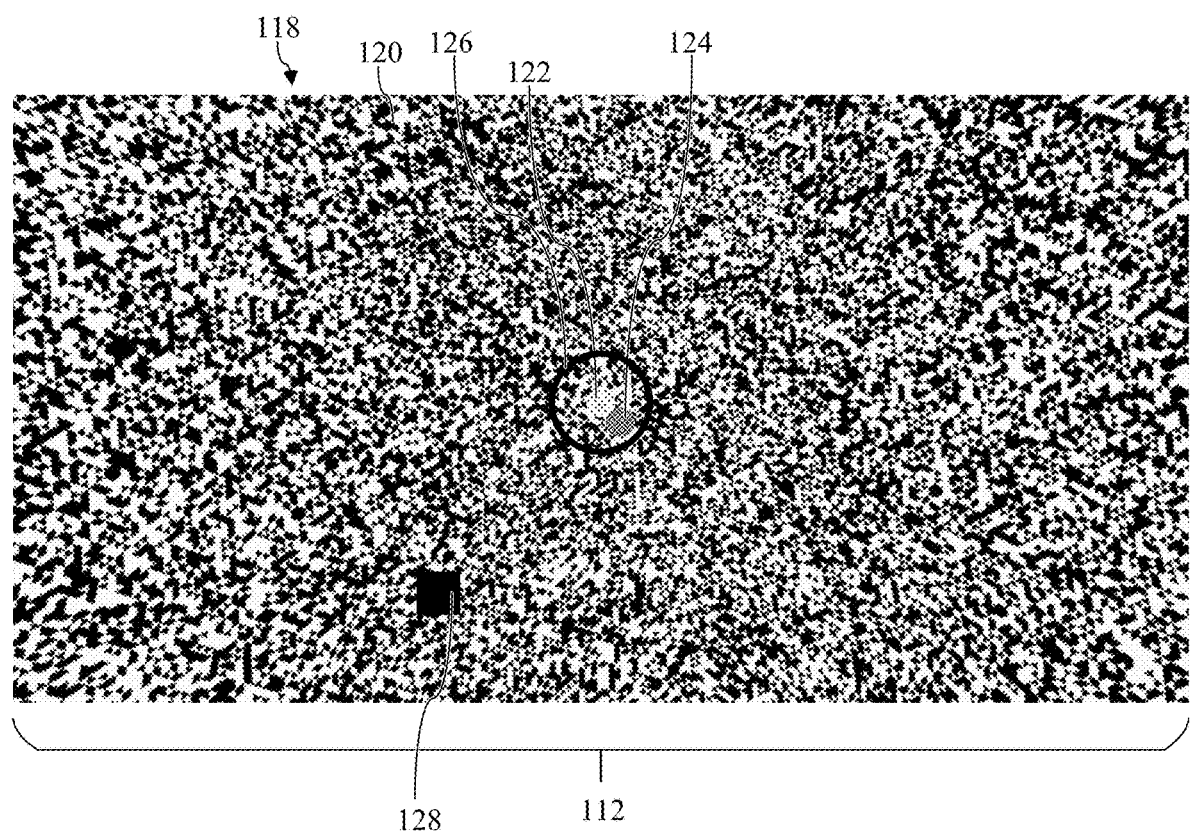

FIG. 2C depicts visual field 112 including a dark stimulus 128 on the lower left side of noisy background 118 to be used in various embodiments of the ON-OFF perimetry visual field test, as discussed herein.

Figure 2D:
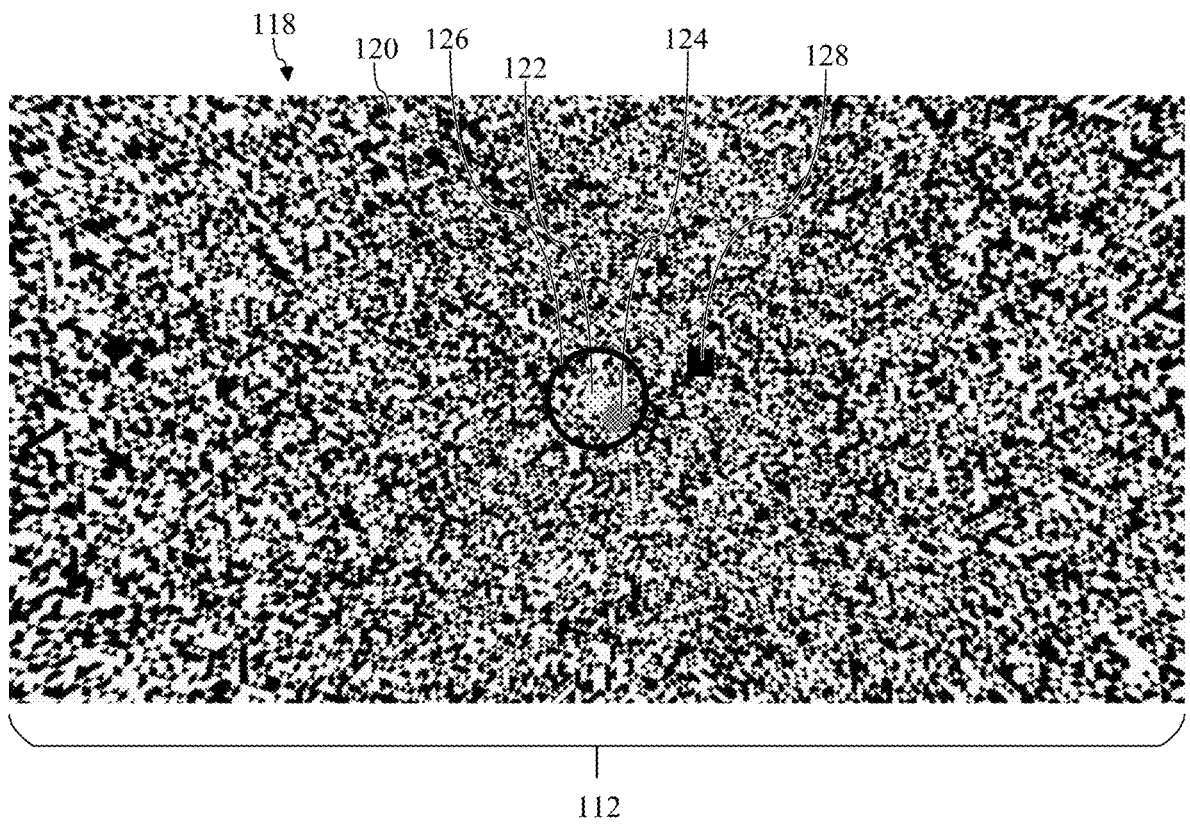

FIG. 2D depicts visual field 112 including dark stimulus 128 on the right side of noisy background 118 to be used in various embodiments of the ON-OFF perimetry visual field test, as discussed herein.

Figure 2E:
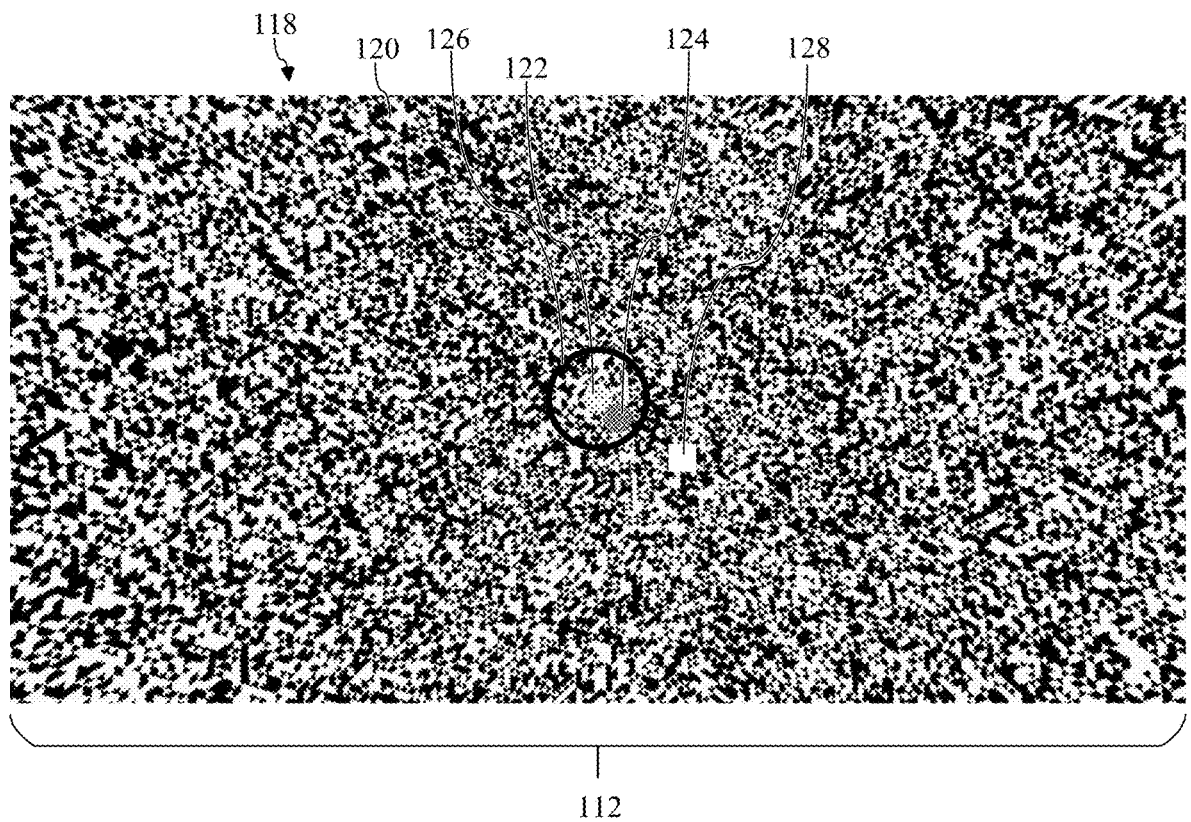

FIG. 2E depicts visual field 112 including light stimulus 112 on the right side of noisy background 118 for use in various embodiments of the ON-OFF perimetry visual field test, as discussed herein.

Figure 2F:
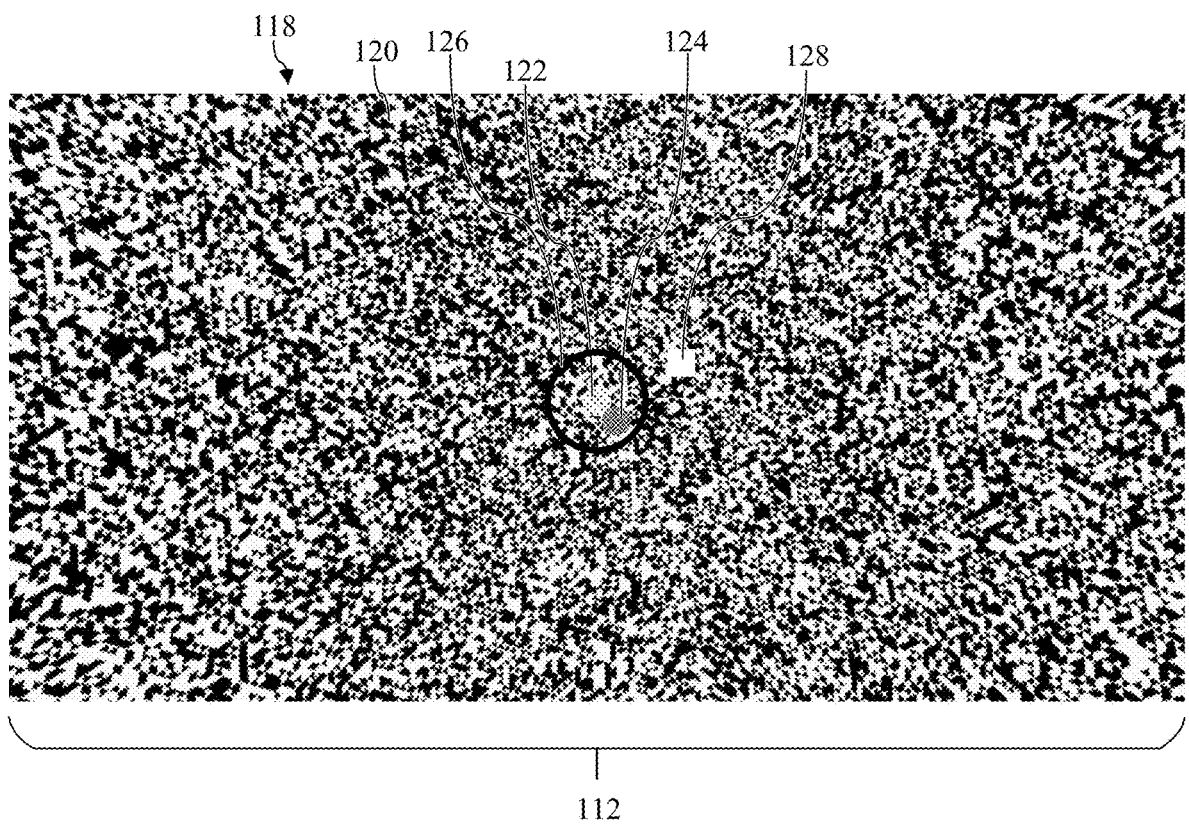

FIG. 2F depicts visual field 112 including light stimulus 112 on the upper right side of noisy background 118 for use in various embodiments of the ON-OFF perimetry visual field test, as discussed herein.

During the ON-OFF perimetry visual field test shown in FIGS. 2A-2F, eye movements may be restricted to the center of visual field 112 within 2.5 degrees for an average patient with normal vision and the restriction may be adjusted based on the patient's performance. For example, restriction may be increased for patients that can maintain excellent fixation and decreased for patients with visual diseases that limit their fixation ability.

Figure 3:
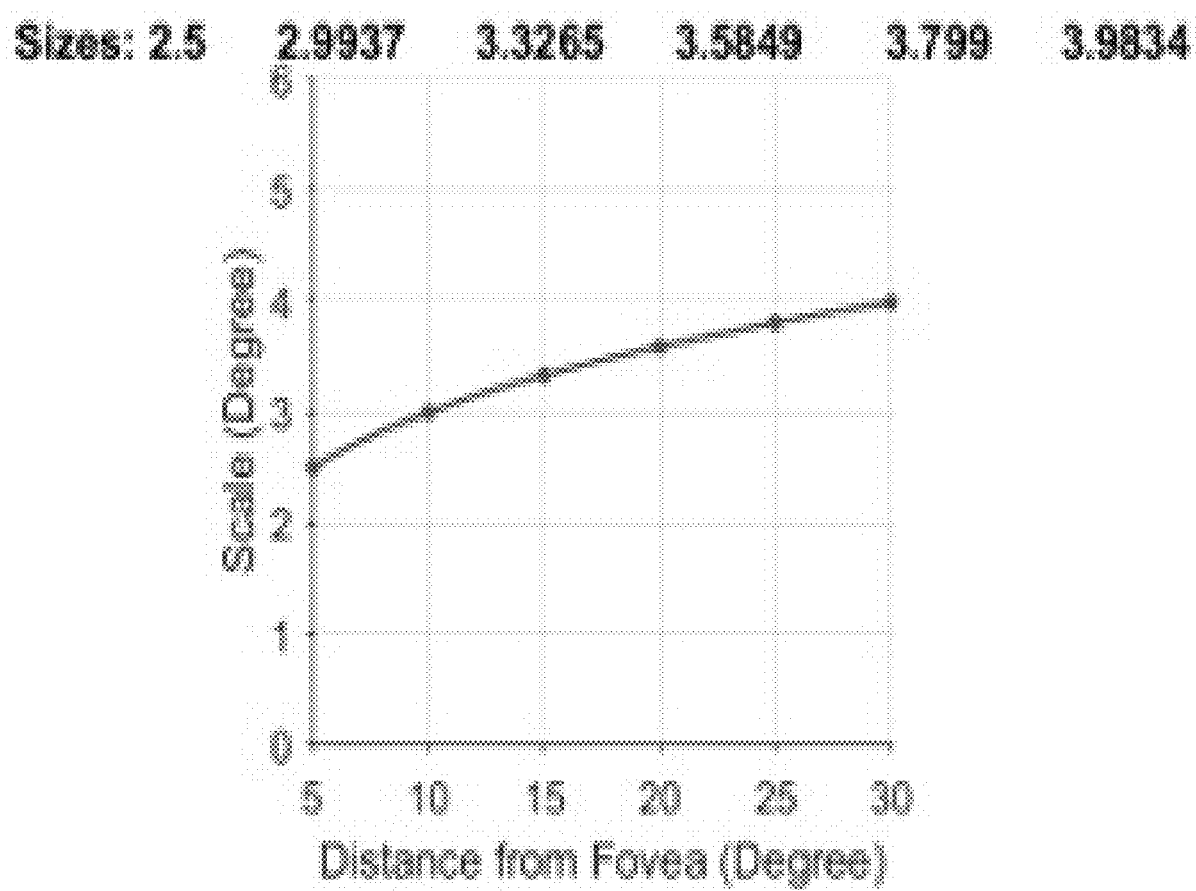
FIG. 3 shows a power function graph, including an x-axis illustrating the relation between the eccentricity distance from the point of fixation at the fovea where the visual acuity is the highest and a y-axis representing a stimulus size, according to embodiments of the disclosure.

As depicted in FIG. 3, and as discussed herein, the size of stimuli 128 may change as a function of eccentricity with a power law relationship ($y=m*(d/5)^x$) defined by two variables: the minimum visible size within central 5-10 degrees (m), and the exponent of the power function (x) that scales visual eccentricity distance in degrees (d).

A Power Law is a functional relationship between two quantities, wherein one quantity varies as a power of the other. In other words, a change in one quantity results in a proportional power change in the other quantity, irrespective of initial quantity size. Such changes can occur through either a power non-linear function or a power linear function (when the power exponent equals 1). When the power is larger than 1, the size increases with the distance from the fixation point. For example, in the power function $y=d^x$, size is 1 for distance 1, 2 for distance 2, and 3 for distance 3, if the power x=1. However, if the power x=2, size is 1 for distance 1, size is $2^2=4$ for distance 2, and $3^2=9$ for distance 3.

In non-limiting examples, the power is generally less than 1. For example, the ON-OFF perimetry visual field tests discussed herein may be run with a minimum size of 2.5 degrees and a power of 0.26. That is, the size is $2.5*(5/5)^{0.26}=2.5$ at a visual eccentricity distance of 5 degrees and $2.5*(30/5)^{0.26}=3.98$ at a visual eccentricity distance of 30 degrees.

In one embodiment, the exponent will make stimulus 128 size increase with visual eccentricity distance. In other words, the size of stimulus 128 depicted in visual field 112 will increase as the distance from the point of fixation (e.g., eye fixation region 122) increases, wherein stimulus 128 is smaller in size for central vision (e.g., inside eye fixation control region 126) and larger in size for peripheral vision (e.g., outside eye fixation control region 126), while keeping the stimulus detection reaction times and percent of correct responses similar for both central and peripheral vision. In another embodiment, the power function may be adjusted to make peripheral stimuli equally visible as central stimuli.

For example, in most tested patients, using a minimum size of 2.5 degrees and a power of 0.26 makes stimuli 128 equally likely to be detected at all visual distances. Alternatively, any type of function or parameter combination (e.g. m from 0.1 to 20 degrees, x from 0 to 2) may be used to make stimuli 128 equally visible at all visual eccentricity distances.

Additionally, or alternatively during the ON-OFF perimetry visual field test, displays 104, 106 of display apparatus 102 may provide 2-dimensional images to each eye that may resemble the real-world projections based on the depth and viewing angle of the patient. This in turn may let the patient have 3D experience in the designed virtual reality environment (e.g., display apparatus 102). Additionally, it is understood that a region of visual field 112 displayed in display apparatus 102 where the patient only sees stimulus 128 larger than aged-similar controls is classified as a scotoma region (i.e. a region with a visual deficit).

Figure 4:
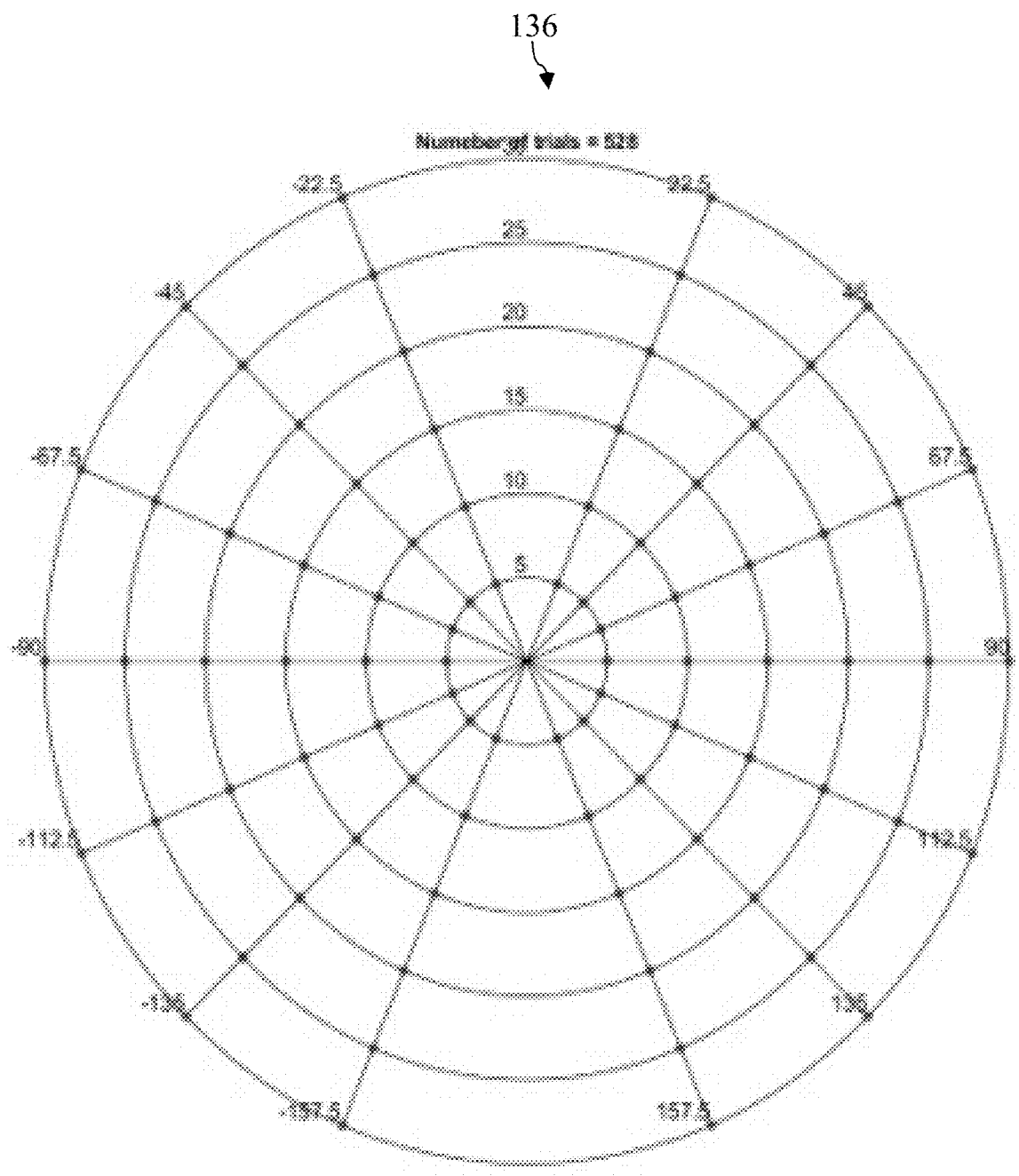
FIG. 4 shows an illustrative view of a sector-based visual field including sectors, where each sector marks the position of the visual field sampled by the stimulus, according to embodiments of the disclosure.

Turning to FIG. 4, a non-limiting example of a sector-based visual field 136 is shown. Sector-based visual field 136 shown in FIG. 4 may correspond to visual field 112. More specifically, sector-based visual field 136 may include a predetermined, anticipated, and/or calculated visual field for a patient undergoing the ON-OFF perimetry visual field test, as discussed herein. Calibration targets 134 and/or stimuli 128 may be displayed in one of a variable number of different sectors contained within a variable number of concentric circles, which cover a variable amount of sector-based visual field 136. Each sector may be sampled a number of different times, and each different sample may display different ratios of dark stimuli and light stimuli during the ON-OFF perimetry visual field test.

In a non-limiting example, the ON-OFF perimetry visual field test may use or depict stimuli 128 in a plurality of the 84 sectors within six concentric circles (see e.g., FIG. 4), which covers between five degrees and thirty degrees of the visual filed. Additionally in a non-limiting example, each sector may be sampled six different times, of which three samples may display dark stimuli 128 and three samples may display light stimuli 128.

Figure 5:
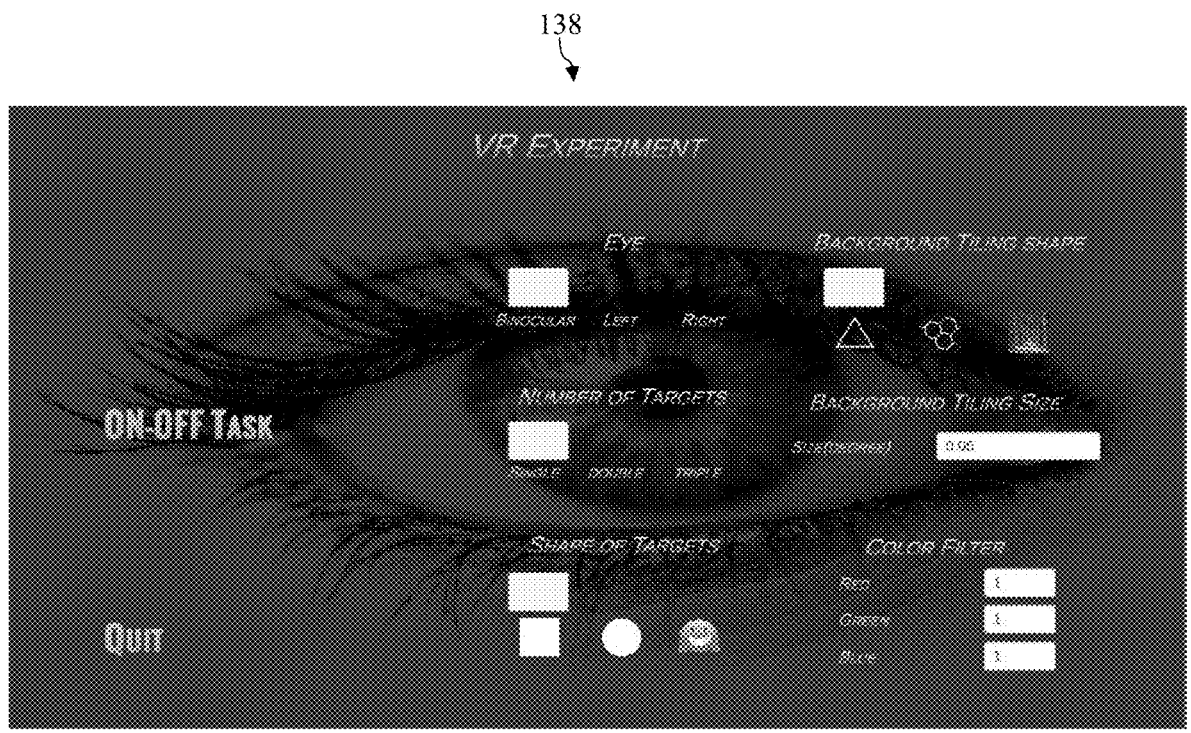
FIGS. 5 and 6 depict various illustrative views of a graphical user interface (GUI) allowing a user of the system of FIG. 1 to adjust operational characteristics relating to the ON-OFF perimetry visual field tests, according to embodiments of the disclosure.
Figure 6:
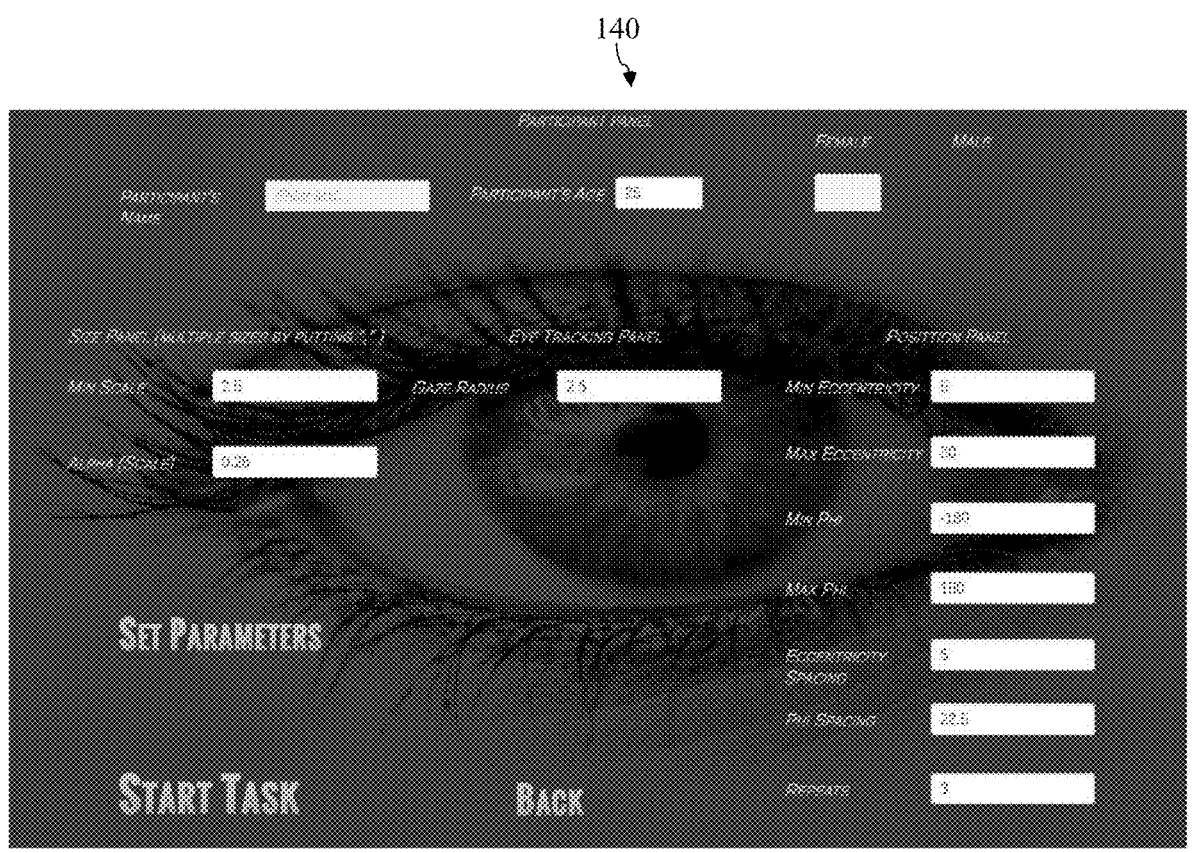

Turning to FIGS. 5 and 6, non-limiting examples of program run/generated by computing device(s) 130 for performing ON-OFF perimetry visual field tests may be shown. More specifically, FIGS. 5 and 6 may depict non-limiting examples of graphical user interfaces (GUI) 138, 140 generated and provided by computing device(s) 130. As shown in the non-limiting GUI 138, 140 examples, a user responsible for testing a patient using system 100 and/or under the ON-OFF perimetry visual field tests discussed herein may adjust various operational parameters, characteristics, and/or tasks of the test. The adjustment of the various operational parameters, characteristics, and/or tasks of the test may make the test customizable, which in turn may improve the results when performing ON-OFF perimetry visual field tests, and/or may more readily identify visual deficits and/or specific eye diseases in a patient during the test. For example, and as shown in FIG. 5, a user may adjust eye-specific testing procedure including whether the test is performed using both eyes (e.g., binocular) or identifying the specific eye in which the test is performed on. A user may also be able to change the tiling shape of background 118 shown in visual field 112, and determine the number of stimuli 128 provided to a patient during the testing. As shown in FIG. 5, a user may also define the size of each tile/shape forming background 118, choose the shape of stimuli 128, and adjust the color filtration of the features (e.g., stimuli 128) included in visual field 112. Turning to FIG. 6, GUI 140 generated by computing device(s) 130 may allow a user to input and/or change, for example, a patient's name, a patient's age, an identify a patient's sex. Additionally, GUI 140 shown in FIG. 6 may allow a user testing a patient to adjust/change a size panel for visual field 112, operational parameters for eye tracking performed by eye tracking system 108 of display apparatus 102 (see, FIG. 1B), and/or parameters (e.g., eccentricity, eccentricity spacing, repeats, etc.) relating to stimuli 128 depicted on visual field 112. Additional operational parameters, characteristics, and/or tasks of the test that may be adjusted using GUI 138, 140 may include, but are not limited to, the stimulus size and contrast, eye fixation limits, and positions sampled in the visual field, stimulus size, number of stimuli, stimulus colors, stimulus contrast, mean luminance, stimulus shape, duration and variations in background tiling size, background tile color, background tile contrast, mean luminance, and background tile shape.

Preliminary Research

Preliminary research tested eight glaucoma subjects (53 to 79 years old), eight age-matched control subjects (59 to 76 years old), and eight young controls (20 to 25 years old). All subjects made more errors when tested with light targets or stimuli, than with dark targets or stimuli. Some subjects with early stages of glaucoma failed to see light stimuli approximately five times more often than dark stimuli (see, FIG. 7).

Figure 8:
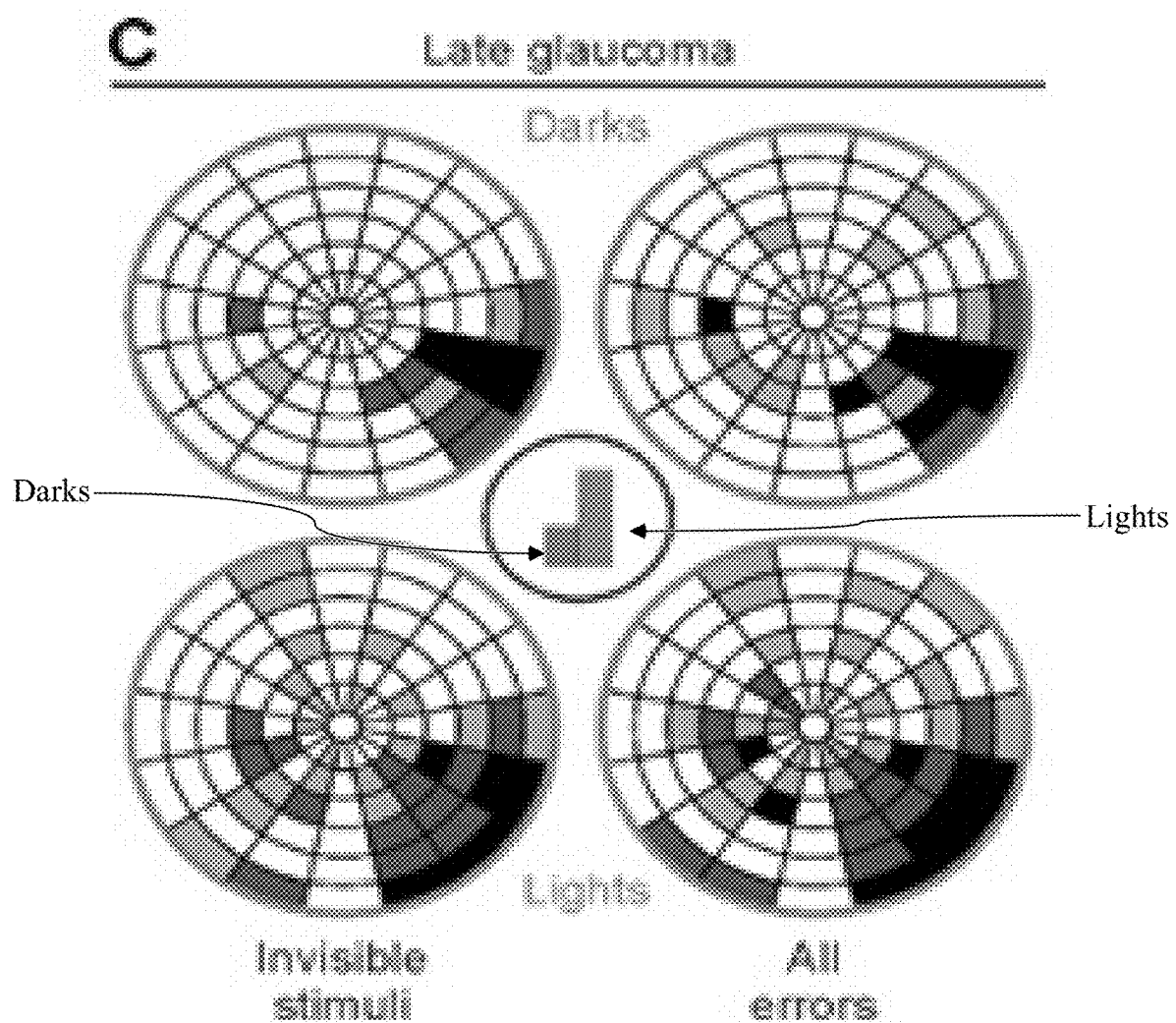
FIG. 8 shows a visual representation of the results of a late glaucoma patient that underwent the ON-OFF perimetry visual field test, according to embodiments of the disclosure.

This indicates a visual deficit more pronounced within the ON-pathway than the OFF-pathway. In contrast, some subjects, notably subjects with advanced glaucoma, failed to see light stimuli approximately two times more often than dark stimuli (FIG. 8). This indicates that, over the progression of the disease, the glaucoma damage on OFF-pathway and ON-pathways become more similar.

The preliminary research results are consistent in showing that dark stimuli are processed faster than light stimuli and that the diseases of the eye, including but not limited to glaucoma, affect both ON-pathway and OFF-pathways. In other words, results indicate that glaucoma affects ON-pathway during the early stages of onset of glaucoma, and as the disease progresses, it starts affecting the OFF-pathway. Early stages of glaucoma may affect ON- more than the OFF-pathways in some patients and OFF-more than ON-pathways in others. Distinguishing between these two possible variations of glaucoma deficits is only possible with perimetry that can measure both ON and OFF visual functions.

Subsequently, as the disease progresses further, the two pathways may become more similarly affected. The disclosed ON-OFF perimetry test will be able to measure the temporal course of ON and OFF visual deficits to overcome the shortcomings of white-on-white perimetry test that only measures deficits in the ON-pathway.

Figure 7:
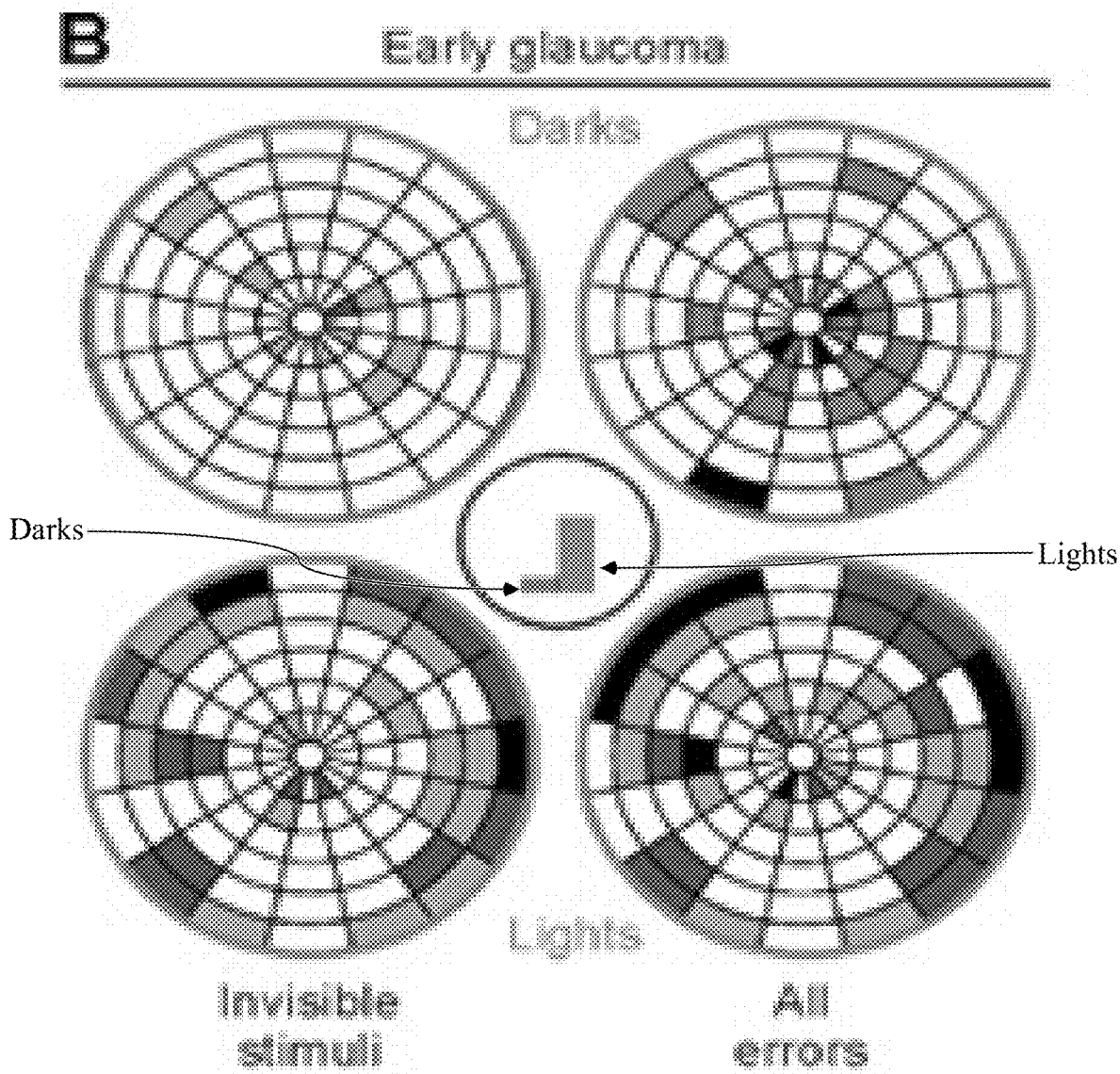
FIG. 7 shows a visual representation of the results of an early glaucoma patient that underwent the ON-OFF perimetry visual field tests, according to embodiments of the disclosure.
Figure 9:
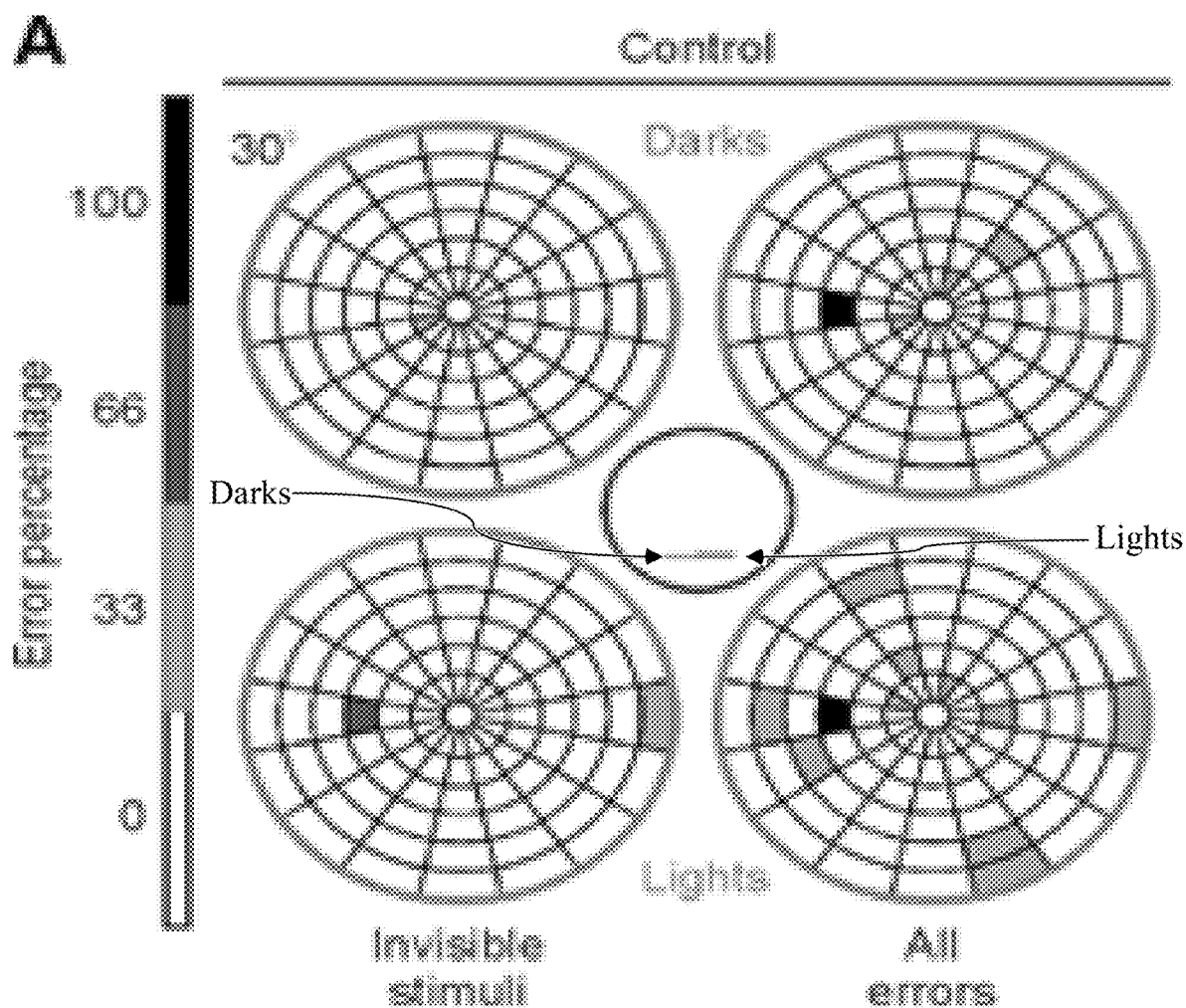
FIG. 9 shows a visual representation of the results of a control patient that underwent the ON-OFF perimetry visual field test, according to embodiments of the disclosure.

Further, among control subjects, the most errors occurred when stimuli were displayed in the blind spot (FIG. 9). Amongst the glaucoma subjects, errors disseminated throughout the visual field, which is consistent with expectations due to the retinal degeneration known to effect glaucoma subjects (FIG. 7).

The results of this preliminary research indicate several advantages to ON-OFF perimetry testing.

First, the results suggest that ON-OFF perimetry will be able to identify ON-OFF functional differences across the entire scope of glaucoma progression, and other similarly situated diseases of the retina and visual pathway.

Second, the results suggest that ON-OFF perimetry will be easier to use than traditional white-on-white perimetry with its user-friendly software comprising of easy to navigate main menu and parameter menu as depicted in FIGS. 5 and 6, respectively.

Third, the results suggest that ON-OFF perimetry will be more comfortable and convenient to use than traditional white-on-white perimetry. ON-OFF perimetry could be administered at home using head-mounted displays. This portable feature of ON-OFF perimetry allows a more comfortable setting for testing and could also help improve compliance since patients may be less reluctant to take the test multiple times to monitor disease progression at home than in the eye clinic.

Figure 10:
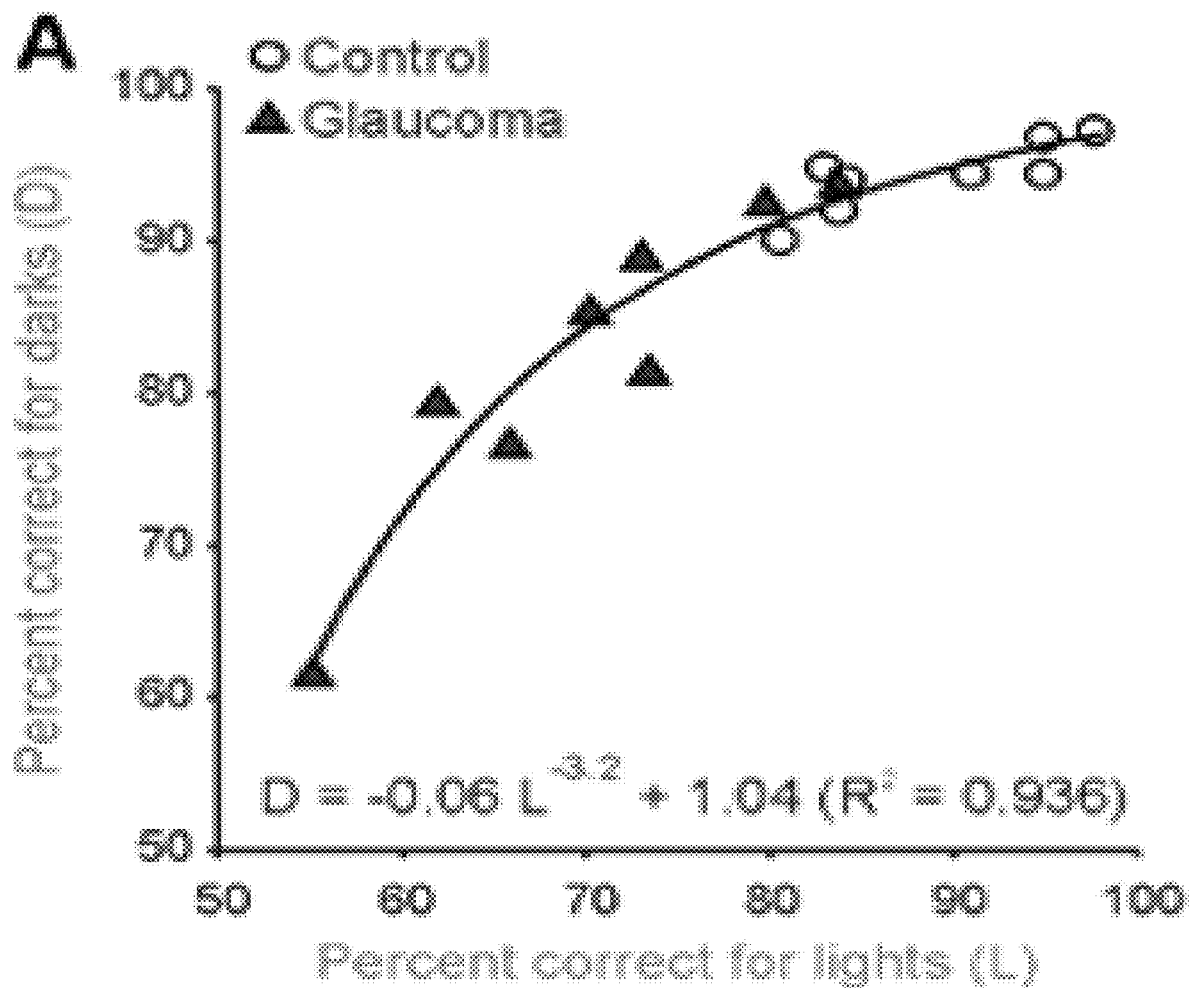
FIG. 10 shows results of the ON-OFF perimetry visual field test as a graphical representation, following a power function, that plots a control patient's percentage of correct responses to light stimuli as a function of their percentage of correct responses to dark stimuli, according to embodiments of the disclosure.

Fourth, the results suggest that a power function ($y=a^x$) defines the relationship between the percentage of correct responses for light stimuli and the percentage of correct responses for dark stimuli. FIG. 10 shows that, within this power function, glaucoma and age-matched individuals slightly overlap.

Figure 11:
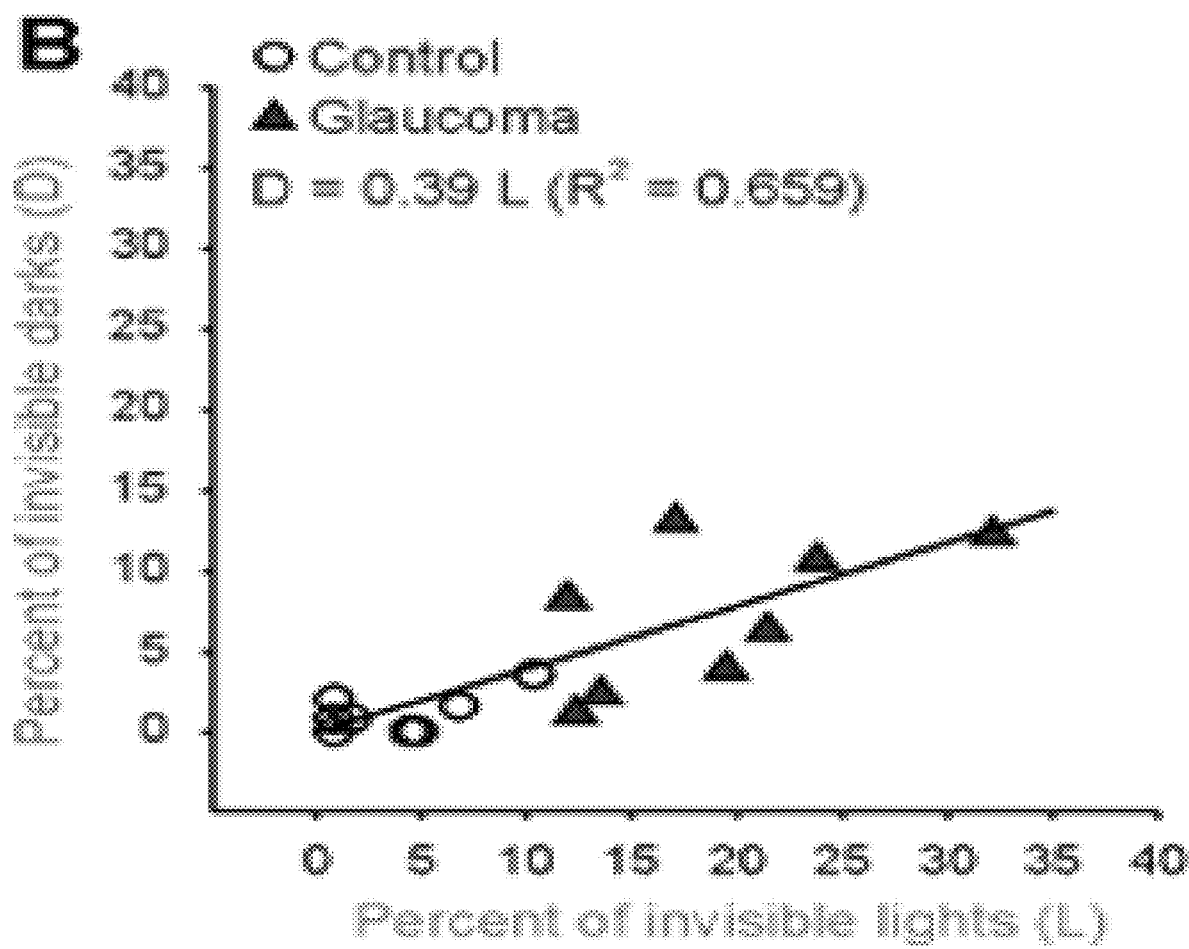
FIG. 11 shows a graphical representation, following a linear function, of the results of the ON-OFF perimetry visual field test, where percentage of correct responses to invisible light stimuli is plotted against the percentage of correct responses to invisible light stimuli, according to embodiments of the disclosure.

FIG. 11 shows that, within this power function, the overlap between glaucoma and age-matched individuals is nearly absent when the analysis is restricted to invisible targets. All age-matched control subjects failed to see less than 12% of the targets. In other words, all age-matched control subjects were able to see at least 88% of the targets.

In contrast, most glaucoma subjects, even those with early stages of the disease, failed to see a higher percentage of the targets. In other words, most glaucoma patients, were able to see less than 88% of the targets.

ON-OFF perimetry test can be further modified and customized by rigorously quantifying alertness based on measurements of reaction time and pupil diameter. This gives the opportunity to dynamically adjust the test to keep alertness at an optimal level and reduce variability in the measurements. For example, over the time course of the test (e.g. 15 minutes or longer), pronounced increases in reaction time (e.g. becoming 1 second slower than in initial trials) or decreases in pupil diameter (e.g. 1 mm smaller than initial trials) are strong indicators that the level of alertness is decreasing due to fatigue, poor motivation or other reasons. Because ON-OFF testing is continuously monitoring pupil diameter and reaction time, it can include an algorithm that generates a warning signal when it detects changes in alertness (e.g. reaction time 1 second slower and pupil diameter 1 mm smaller). The warning signal could be incorporated as a gentle reminder (e.g. "Your level of alertness is decreasing. Would you like to take a break?") or as a beep sound that instructs the patient to pay more attention.

ON-OFF perimetry can be also modified to test the detection of slow-moving stimuli, which are more difficult to see with ON than OFF pathway deficits. The task with moving stimuli is identical to the task except that the target is not a square but a rectangle moving horizontally within the square area of the target in the task.

As expected, deficits measured with standard white-on-white perimetry did not correlate with deficits measure with ON-OFF perimetry. This indicates that the disclosed method of ON-OFF perimetry measures different functional deficits than white-on-white perimetry and is better suited to detect visual deficits in both ON and OFF pathways.

Figure 12:
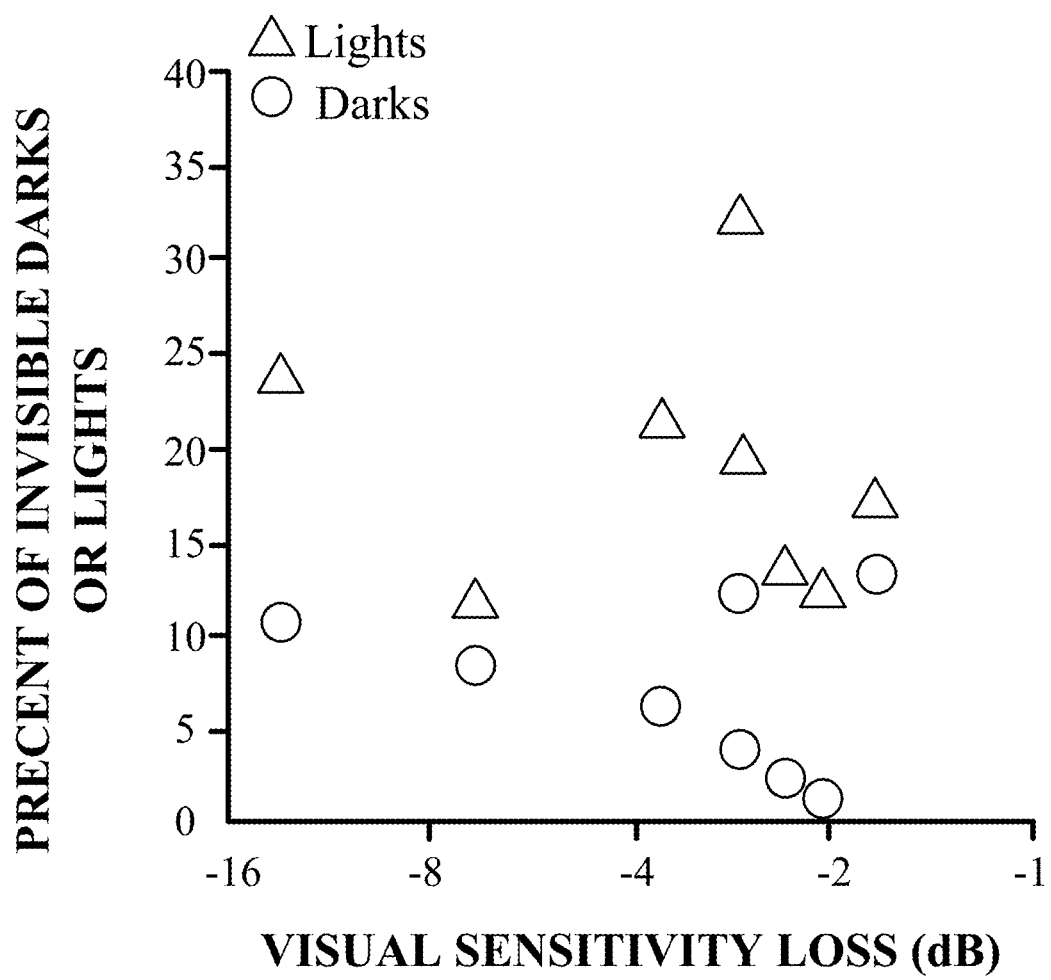
FIG. 12 shows a graphical representation, with no significant correlation, of the results of the ON-OFF perimetry test, according to embodiments of the disclosure. Sensitivity loss measured with standard white-on-white perimetry is plotted against the percentage of correct responses to invisible dark or light stimuli measured with ON-OFF perimetry test.

FIG. 12 depicts a graphical representation, with no significant correlation, of the results of a non-limiting example of an ON-OFF perimetry visual field test as discussed herein, wherein sensitivity loss measured with standard/conventional white-on-white perimetry is plotted against the percentage of correct responses to invisible dark or light stimuli 128 measured with the test discussed herein. The lack of correlation may indicate that the visual deficits detected by ON-OFF perimetry are different and unrelated to the visual deficits detected by white-on-white perimetry tests.

Figure 13:
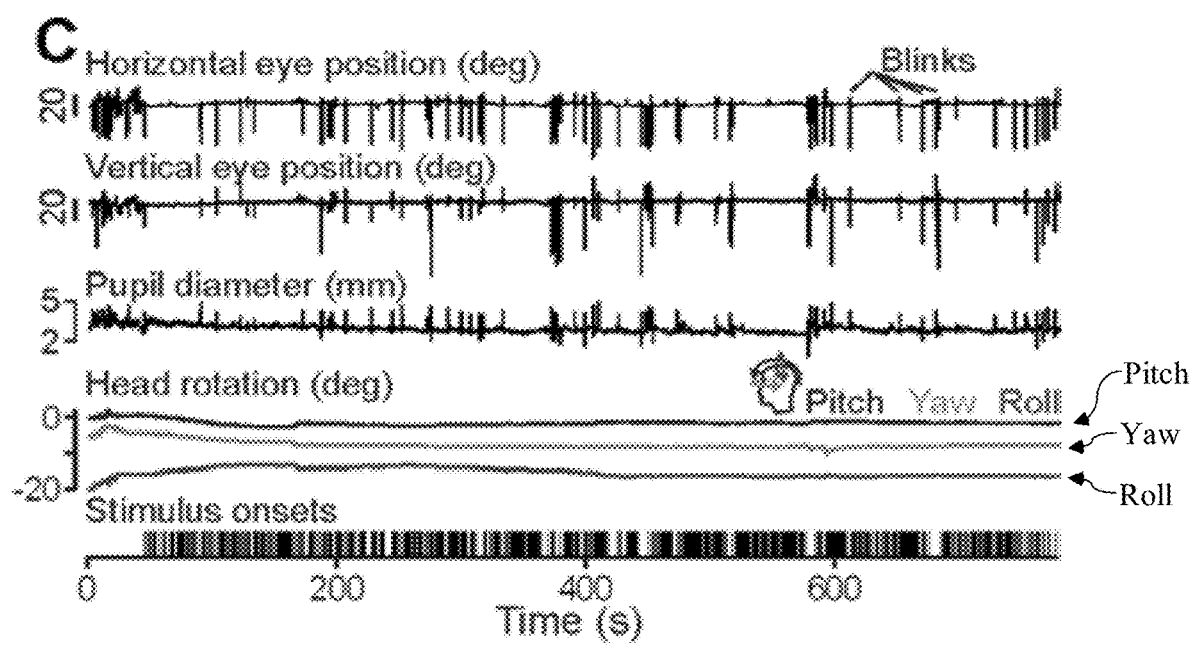
FIG. 13 shows a graphical representation of variables measured, as a function of time, by the system of FIG. 1, including horizontal eye position, vertical eye position, pupil diameter, head rotation, and stimulus onsets, according to embodiments of the disclosure.

Additionally, FIG. 13 depicts graphical representations of variables measured, as a function of time, including horizontal eye position, vertical eye position, pupil diameter, head rotation, and stimulus onsets.

An advantage of the ON-OFF perimetry visual field test discussed herein is its potential to create additional embodiments capable of testing a wide range of visual diseases and conditions. Further fine tuning and customization will enable the test to detect deficits in both eye muscle function and alertness, by analyzing other parameters tested by ON-OFF perimetry. Rigorous quantification of alertness can be achieved by using ON-OFF perimetry to measure reaction time and pupil diameter. Furthermore, the system utilized herein for performing ON-OFF perimetry visual field tests may provide a testing mechanism for both monocular and binocular testing. Additionally, the system and method of performing ON-OFF perimetry visual field test discussed herein may reduce the testing time and/or identify visual deficits in less time than conventional systems/processes. For example, the calibration process discussed herein may be performed in about one (1) minute, while the testing process (e.g., FIGS. 2B-2F) may take approximately 15 minutes in total.

As discussed herein, various systems and components are described as "obtaining" data (e.g., computing device(s) 130 obtaining data from remotes 132, etc.). It is understood that the corresponding data can be obtained using any solution. For example, the corresponding system/component can generate and/or be used to generate the data, retrieve the data from one or more data stores (e.g., a database), receive the data from another system/component, and/or the like. When the data is not generated by the particular system/component, it is understood that another system/component can be implemented apart from the system/component shown, which generates the data and provides it to the system/component and/or stores the data for access by the system/component.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. "Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about," "approximately" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise. "Approximately" as applied to a particular value of a range applies to both values, and unless otherwise dependent on the precision of the instrument measuring the value, may indicate +/−10% of the stated value(s).

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A method for performing an ON-OFF perimetry visual field test, the method comprising:
   directing a patient to visual focus on an eye fixation region depicted in a visual field, the visual field projected to the patient via at least one display of a display apparatus, wherein the visual field is divided into a right side and a left side;
   generating a plurality of stimuli in the visual field to be visually detected by the patient;
   wherein directing further includes:
      providing the patient with a first remote and a second remote, each of the first remote and the second remote in electronic communication with at least one computing device in electronic communication with the display apparatus;
      directing the patient to engage the first remote in response to the patient visually detecting a stimulus of the plurality of stimuli being generated in the left side of the visual field; and
      directing the patient to engage the second remote in response to the patient visually detecting the stimulus of the plurality of stimuli being generated in the right side of the visual field;
   providing the patient a predetermined period of time to engage one of the first remote or engage the second remote in response to visually detecting the stimulus of the plurality of stimuli;
   directing the patient to indicate when the patient visual detects each stimulus of the plurality of stimuli depicted within the visual field; and
   analyzing the patient's indications to diagnose at least one of a retinal disease, a visual cortex disease, or a deficit condition of an eye of the patient.

2. The method of claim 1, wherein analyzing the patient's indications to diagnose at least one of the retinal disease, the visual cortex disease, or the deficit condition of an eye of the patient further includes:
   detecting the at least one of the retinal disease, the visual cortex disease, or the deficit condition of an eye of the patient in response to the patient not engaging the first remote or engaging the second remote in response to the stimulus of the plurality of stimuli being generated in the visual field.

3. The method of claim 1, further comprising:
   tracking eye function of the patient,
   monitoring eye position of the patient,
   monitoring head position of the patient, or
   monitoring pupil diameter of the patient.

4. The method of claim 1, wherein directing the patient to focus on the eye fixation region depicted in the visual field further includes:
   directing the patient to maintain their vision within an eye fixation control region surrounding the eye fixation region, the eye fixation control region defining a central vision for the patient.

5. The method of claim 1, wherein the generated plurality of stimuli includes:
   at least one stimulus having a light color; and
   at least one distinct stimulus having a dark color.

6. The method of claim 1, wherein generating the plurality of stimuli in the visual field to be visually detected by the patient further includes:
   generating a sequence of target stimuli, the sequence of target stimuli superimposed on a background included in the visual field.

7. The method of claim 6, wherein the background is depicted in the visual field to include:
   a first plurality of shapes formed from a first color; and
   a second plurality of shapes formed from a second color, the second color contrasting with the first color of the first plurality of shapes.

8. The method of claim 1, further comprising:
   prior to generating the plurality of stimuli in the visual field, calibrating eye movement of the patient by:
      directing the patient to visual focus on a plurality of calibration targets depicted in the visual field, the plurality of calibration targets moving to a plurality of distinct positions within the visual field; and
      tracking the movement of the patient's eye as it visually focuses on each of the plurality of calibration targets.

9. A non-transitory computer readable storage medium having program instructions stored therein, the program instructions executable by a processor to cause a computing device to perform an ON-OFF perimetry visual field test through the steps of:
   directing a patient to visual focus on an eye fixation region depicted in a visual field, the visual field projected to the patient via at least one display of a display apparatus, wherein the visual field is divided into a right side and a left side;
   calibrating eye movement of the patient by:
      directing the patient to visual focus on a plurality of calibration targets depicted in the visual field, the plurality of calibration targets moving to a plurality of distinct positions within the visual field; and
      tracking the movement of the patient's eye as it visually focuses on each of the plurality of calibration targets, the tracking by one of:
      tracking eye function of the patient,
      monitoring eye position of the patient,
      monitoring head position of the patient, or
      monitoring pupil diameter of the patient;
   generating a plurality of stimuli in the visual field to be visually detected by the patient;
   directing the patient to indicate when the patient visual detects each stimulus of the plurality of stimuli depicted within the visual field; and
   analyzing the patient's indications to diagnose at least one of a retinal disease, a visual cortex disease, or a deficit condition of an eye of the patient.

10. The non-transitory computer readable storage medium of claim 9, wherein the program instructions executable by a processor to perform the step of analyzing the patient's indications to diagnosis at least one of the retinal disease, the visual cortex disease, or the deficit condition of an eye of the patient to further include:
   detecting the at least one of the retinal disease, the visual cortex disease, or the deficit condition of an eye of the patient in response to the patient not engaging a first remote or engaging a second remote in response to the stimulus of the plurality of stimuli being generated in the visual field.

11. The non-transitory computer readable storage medium of claim 9, wherein the program instructions executable by a processor further cause the step of generating a plurality of stimuli in the visual field to include:
   generating a sequence of target stimuli, the sequence of target stimuli superimposed on a background included in the visual field.

12. The non-transitory computer readable storage medium of claim 9, wherein the program instructions executable by a processor further cause the step of generating a plurality of stimuli in the visual field to include:
  directing the patient to maintain their vision within an eye fixation control region surrounding the eye fixation region, the eye fixation control region defining a central vision for the patient.

13. A system for performing an ON-OFF perimetry visual field test, comprising:
  a display apparatus including at least one display; and
  at least one computing device in electronic communication with the display apparatus including the at least one display, the at least one computing device configured to perform the ON-OFF perimetry visual field test on a patient by performing processes including:
    directing a patient to visual focus on an eye fixation region depicted in a visual field, the visual field projected to the patient via at least one display of a display apparatus, wherein the visual field is divided into a right side and a left side, wherein directing further includes:
      providing the patient with a first remote and a second remote, each of the first remote and the second remote in electronic communication with at least one computing device in electronic communication with the display apparatus;
      directing the patient to engage the first remote in response to the patient visually detecting a stimulus of a plurality of stimuli being generated in the left side of the visual field; and
      directing the patient to engage the second remote in response to the patient visually detecting the stimulus of a plurality of stimuli being generated in the right side of the visual field;
    generating a plurality of stimuli in the visual field to be visually detected by the patient;
    providing the patient a predetermined period of time to engage one of the first remote or engage the second remote in response to visually detecting the stimulus of the plurality of stimuli;
    directing the patient to indicate when the patient visual detects each stimulus of the plurality of stimuli depicted within the visual field; and
    analyzing the patient's indications to diagnose at least one of a retinal disease, a visual cortex disease, or a deficit condition of an eye of the patient.

14. The system of claim 13, wherein the at least one computing device further configured to perform the ON-OFF perimetry visual field test on a patient by performing processes including:
  detecting the at least one of the retinal disease, the visual cortex disease, or the deficit condition of an eye of the patient in response to the patient not engaging the first remote or engaging the second remote in response to the stimulus of the plurality of stimuli being generated in the visual field.

15. The system of claim 13, wherein the at least one computing device configured to perform the ON-OFF perimetry visual field test on a patient by performing processes including one of:
  tracking eye function of the patient,
  monitoring eye position of the patient,
  monitoring head position of the patient, or
  monitoring pupil diameter of the patient.

16. The system of claim 13, wherein the at least one computing device configured to perform the ON-OFF perimetry visual field test on a patient by performing processes further including:
  directing the patient to maintain their vision within an eye fixation control region surrounding the eye fixation region, the eye fixation control region defining a central vision for the patient.

17. The system of claim 13, wherein the at least one computing device further configured to perform the ON-OFF perimetry visual field test on a patient by performing processes including the generated plurality of stimuli that includes:
  at least one stimulus having a light color; and
  at least one distinct stimulus having a dark color.

18. The system of claim 13, wherein the at least one computing device further configured to perform the ON-OFF perimetry visual field test on a patient by performing processes including generating the plurality of stimuli in the visual field to be visually detected by the patient that includes:
  generating a sequence of target stimuli, the sequence of target stimuli superimposed on a background included in the visual field.

19. The system of claim 13, wherein the at least one computing device configured to perform the ON-OFF perimetry visual field test on a patient by performing processes including a background depicted in the visual field to further include:
  a first plurality of shapes formed from a first color; and
  a second plurality of shapes formed from a second color, the second color contrasting with the first color of the first plurality of shapes.

20. The system of claim 13, wherein the at least one computing device further configured to perform the ON-OFF perimetry visual field test on a patient by performing processes including further comprising:
  prior to generating the plurality of stimuli in the visual field, calibrating eye movement of the patient by:
    directing the patient to visual focus on a plurality of calibration targets depicted in the visual field, the plurality of calibration targets moving to a plurality of distinct positions within the visual field; and
    tracking the movement of the patient's eye as it visually focuses on each of the plurality of calibration targets.

* * * * *